(12) United States Patent
Cowan et al.

(10) Patent No.: US 10,688,294 B2
(45) Date of Patent: Jun. 23, 2020

(54) PORTABLE FLUID DELIVERY SYSTEM

(71) Applicant: BAYER MEDICAL CARE INC., Indianola, PA (US)

(72) Inventors: Kevin P. Cowan, Allison Park, PA (US); Mark Trocki, Cheswick, PA (US); Arthur E. Uber, III, Pittsburgh, PA (US)

(73) Assignee: BAYER HEALTHCARE LLC, Indianola, PA (US)

( * ) Notice: Subject to any disclaimer, the term of this patent is extended or adjusted under 35 U.S.C. 154(b) by 515 days.

(21) Appl. No.: 14/897,990

(22) PCT Filed: Jun. 13, 2014

(86) PCT No.: PCT/US2014/042310
§ 371 (c)(1),
(2) Date: Dec. 11, 2015

(87) PCT Pub. No.: WO2014/201358
PCT Pub. Date: Dec. 18, 2014

(65) Prior Publication Data
US 2016/0158519 A1    Jun. 9, 2016

Related U.S. Application Data

(60) Provisional application No. 61/835,131, filed on Jun. 14, 2013, provisional application No. 61/840,818, filed on Jun. 28, 2013.

(51) Int. Cl.
*A61M 39/10* (2006.01)
*A61M 39/16* (2006.01)
(Continued)

(52) U.S. Cl.
CPC ........ *A61M 39/1011* (2013.01); *A61M 5/007* (2013.01); *A61M 39/10* (2013.01);
(Continued)

(58) Field of Classification Search
CPC ............ A61M 39/1011; A61M 39/105; A61M 39/20; A61M 39/10; A61M 39/12;
(Continued)

(56) References Cited

U.S. PATENT DOCUMENTS 926,755 A    7/1909  Locke
2,287,746 A  6/1942  Morton
(Continued)

FOREIGN PATENT DOCUMENTS

CA    1126117 A    6/1982
CA    2574551 A1   7/2008
(Continued)

OTHER PUBLICATIONS

The International Preliminary Report on Patentability dated Apr. 22, 2014 from corresponding PCT Application No. PCT/US2012/060978 filed Oct. 19, 2012.
(Continued)

*Primary Examiner* — Jenna Zhang
(74) *Attorney, Agent, or Firm* — David Schramm; Joseph Kent; James Stevenson

(57) ABSTRACT

A fluid delivery system includes a first container configured for storing a first fluid therein and a second container configured for storing a second fluid therein, wherein the second fluid is different from the first fluid. The fluid delivery system further includes at least one pump configured for delivering under pressure one or both of the first and second fluids. At least one valve is provided for selectively delivering one or both of the first and second fluids to the pump. The first and second containers, the pump, and the valve are contained within a cartridge that is removably insertable into a cartridge carrier of the fluid delivery system.

20 Claims, 37 Drawing Sheets

(51) Int. Cl.
*A61M 5/00* (2006.01)
*A61M 39/20* (2006.01)
*A61M 5/142* (2006.01)
*A61M 5/14* (2006.01)
*A61M 39/12* (2006.01)
*A61M 39/26* (2006.01)
*A61M 39/00* (2006.01)

(52) U.S. Cl.
CPC .......... *A61M 39/105* (2013.01); *A61M 39/20* (2013.01); *A61M 5/1413* (2013.01); *A61M 5/14212* (2013.01); *A61M 5/14232* (2013.01); *A61M 39/12* (2013.01); *A61M 39/26* (2013.01); *A61M 2039/0018* (2013.01); *A61M 2039/167* (2013.01); *A61M 2205/12* (2013.01); *A61M 2205/123* (2013.01); *A61M 2205/128* (2013.01); *A61M 2205/3389* (2013.01)

(58) Field of Classification Search
CPC .. A61M 39/26; A61M 5/007; A61M 5/14212; A61M 5/14232; A61M 5/1413; A61M 2039/0018; A61M 2205/123; A61M 2205/128; A61M 2205/3389
See application file for complete search history.

(56) References Cited

U.S. PATENT DOCUMENTS

| | | |
|---|---|---|
| 2,731,053 A | 1/1956 | Lockhart |
| 2,780,243 A | 2/1957 | Williams et al. |
| 2,798,487 A | 7/1957 | Ferguson |
| 2,938,238 A | 5/1960 | Gewecke et al. |
| 2,997,043 A | 8/1961 | Flynn |
| 3,164,279 A | 1/1965 | Towns |
| 3,658,061 A | 4/1972 | Hall |
| 3,835,862 A | 9/1974 | Villari |
| 3,909,910 A | 10/1975 | Rowe et al. |
| 3,986,508 A | 10/1976 | Barrington |
| 3,987,930 A | 10/1976 | Fuson |
| 4,019,512 A | 4/1977 | Tenczar |
| 4,022,205 A | 5/1977 | Tenczar |
| 4,106,654 A | 8/1978 | Jones |
| 4,123,091 A | 10/1978 | Cosentino et al. |
| 4,187,846 A | 2/1980 | Carminucci et al. |
| 4,194,509 A | 3/1980 | Ferguson et al. |
| 4,227,615 A | 10/1980 | Flick |
| 4,227,715 A | 10/1980 | Kirchmeyr |
| 4,230,231 A | 10/1980 | Burnett et al. |
| 4,340,148 A | 7/1982 | Beckham |
| 4,360,969 A | 11/1982 | Collier |
| 4,366,816 A | 1/1983 | Bayard et al. |
| 4,369,779 A | 1/1983 | Spencer |
| 4,398,757 A | 8/1983 | Floyd et al. |
| 4,402,420 A | 9/1983 | Chernack |
| 4,433,973 A | 2/1984 | Kurtz et al. |
| 4,450,624 A | 5/1984 | Collier |
| 4,482,347 A | 11/1984 | Borsanyi |
| 4,511,359 A | 4/1985 | Vaillancourt |
| 4,551,146 A | 11/1985 | Rogers |
| 4,559,043 A | 12/1985 | Whitehouse et al. |
| 4,579,823 A | 4/1986 | Ryder |
| 4,624,664 A | 11/1986 | Peluso et al. |
| 4,636,204 A | 1/1987 | Christopherson et al. |
| 4,775,369 A | 10/1988 | Schwartz |
| 4,778,447 A | 10/1988 | Velde et al. |
| 4,795,426 A | 1/1989 | Jones |
| 4,810,241 A | 3/1989 | Rogers |
| 4,828,557 A | 5/1989 | Persidsky |
| 4,854,836 A | 8/1989 | Borsanyi |
| 4,883,641 A | 11/1989 | Wicks et al. |
| 4,950,260 A | 8/1990 | Bonaldo |
| 4,981,469 A | 1/1991 | Whitehouse et al. |
| 5,049,047 A | 9/1991 | Polaschegg et al. |
| 5,057,088 A | 10/1991 | Narayanan et al. |
| 5,088,984 A | 2/1992 | Fields |
| 5,098,395 A | 3/1992 | Fields |
| 5,171,229 A | 12/1992 | McNeil et al. |
| 5,184,742 A | 2/1993 | DeCaprio et al. |
| 5,221,267 A | 6/1993 | Folden |
| 5,251,873 A | 10/1993 | Atkinson et al. |
| 5,280,809 A | 1/1994 | Tive |
| 5,281,111 A | 1/1994 | Plambeck et al. |
| 5,292,308 A | 3/1994 | Ryan |
| 5,340,359 A | 8/1994 | Segura Badia |
| 5,382,242 A | 1/1995 | Horton et al. |
| 5,413,280 A | 5/1995 | Taylor |
| 5,482,171 A | 1/1996 | Palmer |
| 5,494,036 A | 2/1996 | Uber, III et al. |
| 5,498,253 A | 3/1996 | Aswad et al. |
| 5,551,850 A | 9/1996 | Williamson et al. |
| 5,569,181 A | 10/1996 | Heilman et al. |
| 5,620,433 A | 4/1997 | Aswad et al. |
| 5,739,508 A | 4/1998 | Uber, III |
| 5,746,718 A | 5/1998 | Steyn |
| 5,785,691 A | 7/1998 | Vetter et al. |
| 5,803,510 A | 9/1998 | Dorsey, III et al. |
| 5,806,519 A | 9/1998 | Evans, III et al. |
| 5,840,026 A | 11/1998 | Uber, III et al. |
| 5,843,037 A | 12/1998 | Uber, III |
| 5,853,096 A | 12/1998 | Bartur et al. |
| 5,913,434 A | 6/1999 | Fukuhara et al. |
| 5,934,496 A | 8/1999 | Mogard et al. |
| 5,964,583 A | 10/1999 | Danby |
| 5,972,292 A | 10/1999 | Demeo |
| 6,077,259 A | 6/2000 | Caizza et al. |
| 6,164,279 A | 12/2000 | Tweedle |
| 6,261,270 B1 | 7/2001 | Gault et al. |
| 6,306,117 B1 | 10/2001 | Uber, III |
| 6,339,718 B1 | 1/2002 | Zatezalo et al. |
| 6,511,472 B1 | 1/2003 | Hayman et al. |
| 6,666,839 B2 | 12/2003 | Utterberg et al. |
| 6,669,681 B2 | 12/2003 | Jepson et al. |
| 6,679,529 B2 | 1/2004 | Johnson et al. |
| 6,814,726 B1 | 11/2004 | Lauer |
| 6,821,267 B2 | 11/2004 | Veillon et al. |
| 6,869,425 B2 | 3/2005 | Briggs et al. |
| 6,911,025 B2 | 6/2005 | Miyahara |
| 6,981,960 B2 | 1/2006 | Cho et al. |
| 7,022,256 B2 | 4/2006 | Uegami et al. |
| 7,040,598 B2 | 5/2006 | Raybuck |
| 7,070,589 B2 | 7/2006 | Ebner et al. |
| 7,083,605 B2 | 8/2006 | Miyahara |
| 7,097,209 B2 | 8/2006 | Unger et al. |
| 7,241,285 B1 | 7/2007 | Dikeman |
| 7,252,308 B2 | 8/2007 | Thilly |
| 7,374,555 B2 | 5/2008 | Heinz et al. |
| 7,452,349 B2 | 11/2008 | Miyahara et al. |
| 7,481,795 B2 | 1/2009 | Thompson et al. |
| 7,569,047 B2 | 8/2009 | Utterberg |
| 7,618,412 B2 | 11/2009 | Chernack |
| 7,713,250 B2 | 5/2010 | Harding et al. |
| 7,731,155 B2 | 6/2010 | Funamura et al. |
| 7,740,288 B2 | 6/2010 | Mantell |
| 7,918,243 B2 | 4/2011 | Diodati et al. |
| 7,938,454 B2 | 5/2011 | Buchanan et al. |
| 8,007,487 B2 | 8/2011 | Patrick et al. |
| 8,012,144 B2 | 9/2011 | Moberg |
| 8,038,667 B2 | 10/2011 | Racz et al. |
| 8,062,009 B2 | 11/2011 | Cueni |
| 8,133,035 B2 | 3/2012 | Wolff |
| 8,140,274 B2 | 3/2012 | Gagel et al. |
| 8,147,464 B2 | 4/2012 | Spohn et al. |
| 8,157,547 B2 | 4/2012 | Hermanus Oude Vrielink et al. |
| 8,287,724 B2 | 10/2012 | Slepicka et al. |
| 8,308,456 B2 | 11/2012 | Moubayed |
| 8,343,128 B2 | 1/2013 | Nagao et al. |
| 8,360,757 B2 | 1/2013 | Knauper et al. |
| 9,408,971 B2 | 8/2016 | Carlyon et al. |
| 2001/0016704 A1 | 8/2001 | Zadno-Azizi et al. |
| 2002/0010437 A1 | 1/2002 | Lopez et al. |
| 2002/0093192 A1 | 7/2002 | Matkovich |
| 2004/0111078 A1 | 6/2004 | Miyahara |
| 2004/0227120 A1 | 11/2004 | Raybuck |

(56) References Cited

U.S. PATENT DOCUMENTS

| | | | |
|---|---|---|---|
| 2005/0090805 A1 | 4/2005 | Shaw et al. | |
| 2005/0113754 A1* | 5/2005 | Cowan | A61M 5/31511 604/131 |
| 2008/0071219 A1 | 3/2008 | Rhinehart et al. | |
| 2008/0071220 A1 | 3/2008 | Rhinehart et al. | |
| 2008/0097342 A1 | 4/2008 | Gordin | |
| 2008/0177250 A1 | 7/2008 | Howlett et al. | |
| 2009/0102192 A1 | 4/2009 | Ziman | |
| 2009/0163890 A1* | 6/2009 | Clifford | A61B 1/227 604/514 |
| 2009/0171316 A1* | 7/2009 | Patrick | A61B 8/00 604/512 |
| 2009/0182309 A1 | 7/2009 | Muffly | |
| 2009/0216192 A1 | 8/2009 | Schriver et al. | |
| 2010/0049170 A1 | 2/2010 | Solomon et al. | |
| 2010/0056975 A1 | 3/2010 | Dale et al. | |
| 2010/0249586 A1 | 9/2010 | Cocker et al. | |
| 2011/0001317 A1* | 1/2011 | Chang | A61M 1/008 285/148.2 |
| 2011/0049866 A1 | 3/2011 | Trombley, III et al. | |
| 2011/0054440 A1 | 3/2011 | Lewis | |
| 2011/0240158 A1 | 10/2011 | Py | |
| 2011/0313394 A1 | 12/2011 | Bobo, Sr. | |
| 2012/0148415 A1 | 6/2012 | Brueckner et al. | |
| 2013/0033034 A1 | 2/2013 | Trombley, III et al. | |
| 2013/0079581 A1 | 3/2013 | Agamaite et al. | |
| 2013/0123567 A1 | 5/2013 | Agamaite et al. | |
| 2013/0281940 A1* | 10/2013 | Gelblum | A61M 5/2425 604/214 |
| 2013/0331634 A1 | 12/2013 | Kaintz et al. | |
| 2013/0331635 A1 | 12/2013 | Hoffman et al. | |
| 2014/0191501 A1* | 7/2014 | Brugger | F16L 35/00 285/120.1 |
| 2014/0228762 A1* | 8/2014 | Capone | F04B 49/06 604/152 |
| 2015/0034194 A1* | 2/2015 | Uber, III | F16L 25/00 137/797 |

FOREIGN PATENT DOCUMENTS

| | | | |
|---|---|---|---|
| DE | 3838689 C1 | 6/1990 | |
| DE | 4037797 C1 | 2/1992 | |
| EP | 0503670 A2 | 9/1992 | |
| EP | 1331020 A1 | 7/2003 | |
| EP | 2275161 A1 | 1/2011 | |
| EP | 1834664 B1 | 5/2013 | |
| FR | 2594496 A1 | 8/1987 | |
| FR | 2847342 A1 | 5/2004 | |
| GB | 2020735 A | 11/1979 | |
| JP | 2003210574 A | 7/2003 | |
| WO | 9103404 A1 | 3/1991 | |
| WO | WO-2008086631 A1 * | 7/2008 | A61M 1/285 |
| WO | 2013043868 A1 | 3/2013 | |
| WO | 2013059563 A1 | 4/2013 | |

OTHER PUBLICATIONS

The International Search Report and Written Opinion of related PCT Application No. PCT/US2014/044500, dated Nov. 4, 2014.
The International Search Report for corresponding PCT Application No. PCT/US2012/060978, dated Feb. 5, 2013.
The Supplementary European Search Report dated Feb. 16, 2015 from corresponding EP Application No. EP12842335.
Allpure; Technologies Inc., "Takeone Aseptic Sampling System Brochure", 2010.
Applied; Bioprocess Containers., "Single-Use Bags 50 to 500 Liters Catalog", Jun. 2010.
"Asepti-Quik S Connector Catalog", May 2012.
Bard; Access Systems., "Site-Scrub IPA Device", http://www.bardaccess.com/products/procedural/site-scrub-ipa.(last visited Sep. 23, 2016), 2012.
Colder; Products Company., "AseptiQuik X Connector Catalog", Oct. 2012.
Colder; Products Company., "Connection Solutions for Biopharmaceutical Processes", 2012.
Comar., "DoseGuard Valved Bottle Adapter System Brochure", Apr. 18, 2013.
GE; Healthcare., "ReadyMate Disposable Aseptic Connectors, Operation Manual", Jul. 2009.
"International Preliminary Report on Patentability and Written Opinion from PCT Application No. PCT/US2014/042310", dated Dec. 15, 2015.
"International Preliminary Report on Patentability, Written Opinion, and International Search Report from PCT/US2014/042310 dated Dec. 15, 2015".
"International Search Report from PCT/US2015/042310", dated Dec. 19, 2014.
Minivalves., "Catalog Valves", http://www.minivalve.com/newsite/index.php—last visited Sep. 23, 2016.
Saint-Gobain Performance Plastics., "Pure Fit SC True Sterile Connections . . . Outside the Clean Room Catalog", 2008.
"Extended European Search Report and Written Opinion from EP14810311", dated Nov. 22, 2016.
"International Preliminary Report on Patentability from PCT Application No. PCT/US2015/010825", dated Jul. 21, 2016.
"International Search Report and Written Opinion from corresponding PCT App. No. PCT/US2015/010825", dated Apr. 10, 2015.
"International Search Report in PCT Application No. PCT/US2014/044500", dated Nov. 4, 2014.
The International Preliminary Report on Patentability dated Dec. 19, 2014 from corresponding PCT Application No. PCT/US14/42310.
Asepti-Quik S Connector Catalog, May 2010.
Hadaway, Lynn, Needleless Connectors: A Primer on Terminology, Journal of Infusion Nursing, Jan./Feb. 2010, 33(1): 22-31.
UFP; Technologies., "BioShell Suspension Pack Brochure", accessed online on May 7, 2013.
Ultraport Swabbable Port Stopcocks, B. Braun Sharing Expertise, accessed online on Apr. 14, 2014.

* cited by examiner

PORTABLE FLUID DELIVERY SYSTEM

CROSS-REFERENCE TO RELATED APPLICATIONS

The present application is a U.S. national stage filing under 35 U.S.C. § 371 of International Application No. PCT/US2014/042310, filed Jun. 13, 2014, which claims priority to U.S. Provisional Patent Application No. 61/835,131, entitled "Portable Fluid Delivery System", filed on Jun. 14, 2013, and U.S. Provisional Patent Application No. 61/840,818, entitled "Sterility Retaining Medical Connector Assembly and Method", filed Jun. 28, 2013, the disclosures of each of which are incorporated herein in their entirety.

BACKGROUND OF THE DISCLOSURE

1. Field of the Disclosure

The present disclosure is directed to medical fluid delivery applications and, particularly, to a portable fluid delivery system for delivering one or more medical fluids and a connector assembly therefor.

2. Description of Related Art

Current medical imaging practice uses a combination of a medical fluid injector and an imaging device to visualize the inside of a patient's body. In certain procedures, a physician maneuvers a catheter to a desired blood vessel, and electromagnetic-absorbing or radiation emitting contrast solution is injected so that the contrast solution, commonly referred to as "contrast", becomes clearly visible against the background of the surrounding tissue.

Using the resultant image, a physician makes a diagnosis and determines appropriate treatment. In interventional procedures, treatment is performed using injection catheters, atherectomy devices, stents, or any one of many interventional devices. Often, the interventional treatment is performed during the angiographic procedure, although sometimes treatment is performed at a later time.

During certain procedures, in addition to contrast, it is common to inject saline to flush the contrast from the catheter. This keeps the catheter lumen open (unclotted), and/or acts as a fluid path for measuring blood pressure. In certain embodiments, the physician performs the injections by hand. However, it may be difficult for a human to inject a fluid at a steady rate, especially for slow rates (ml/min) extending more than a minute. Motion at a slow rate suffers from stick-slip friction in the syringe, and it takes prolonged concentration to maintain a steady injection rate for extended time periods during the procedure. There is significant risk of accidental jerking or bolus injection that either wastes drug or causes it to reflux into the aorta and travel elsewhere in the body. Also, as syringes are connected and disconnected, the plunger can be unintentionally bumped and a bolus of drug injected into the patient or expelled into the environment. Additionally, the changeover time from drug syringe to saline syringe causes an uncontrolled break in therapy injection. As the drug is susceptible to clump formation or crystallization if agitated, manually connecting and disconnecting the syringe provides opportunities for agitation and clumping/crystallizing.

For certain procedures, powered injectors are used to inject the contrast because of its high viscosity and the high pressures required to drive contrast through small catheter diameters. Powered injectors can, for example, develop pressures up to 1200 psi in such injections. The pressure range used in such injections is well above the pressure a person can practically develop via hand injection. U.S. Pat. Nos. 5,494,036, 6,339,718, 5,843,037, 5,840,026, 5,806,519, 5,739,508, and 5,569,181, assigned to the assignee of the present disclosure, which are incorporated herein by reference, disclose the use of powered injector systems that are capable of injecting contrast, saline, and other fluids, either at the same time or in sequence.

One difficulty with such currently available powered injectors is that they require a complex fluid path set to deliver the one or more fluids from a storage container to the patient. Typically, such a fluid path set includes a plurality of fluid lines that are interconnected by one or more connectors and valves. In many cases, a new fluid path set must be assembled for each new patient. Additionally, one or more fluid storage containers are separately provided to the fluid delivery device and must be connected therewith prior to the injection procedure. The assembly process is laborious and time consuming, and increases the risk that some of the fluid may be spilled, aerosolized, or otherwise contaminated. Conventional medical connectors for use with powered injectors require the user to ensure that proper sterilization precautions are taken each time a new connection is made. There exists a significant risk of contamination due to human error in handling the connectors. Furthermore, because conventional medical connectors for use with powered injectors do not have reusable components, large stockpiles of medical connectors must be kept on premises, which increases storage costs and per procedure costs. Accordingly, a need exists for an improved fluid delivery system and a connector assembly therefor.

SUMMARY OF THE DISCLOSURE

While manual and powered injectors are known in the medical field, improved fluid delivery systems are desired. In view of certain disadvantages of the existing manual and powered injection mechanisms, there is a need in the art for an injection device that enables precise dosing of contrast and/or saline. There is an additional need for an injection system having a simplified connection with a fluid path set for delivering the fluid to the patient. A further need exists in the art for an injection system that reduces the risk that some of the fluid may be spilled, aerosolized, or otherwise contaminated. An additional need exists for a portable fluid delivery system having one or more of the above-noted advantages.

In accordance with one embodiment, a cartridge for a fluid delivery system is provided where the cartridge may include a first fluid container configured for storing a first fluid therein and a second fluid container configured for storing a second fluid therein, where the second fluid may be different from the first fluid. The cartridge may further include at least one pump configured for delivering under pressure one or both of the first fluid and the second fluid, and at least one valve configured for selectively delivering one or both of the first fluid and the second fluid to the pump. The first and second containers, the at least one pump, and the at least one valve may be received within an outer shell of the cartridge. The cartridge may be removably engagable with the fluid delivery system.

In accordance with a further embodiment, the at least one pump further may include a first pump in fluid communication with the first fluid container for delivering under pressure the first fluid and a second pump in fluid communication with the second fluid container for delivering under pressure the second fluid. Additionally, the at least one valve may have a plurality of states for selectively allowing a flow of the first fluid, the second fluid or both the first fluid and the second fluid through the at least one valve. In one embodiment, the at least one valve may include (1) a first state where the flow of the first fluid and the second fluid through the at least one valve is closed, (2) a second state where the flow of the first fluid through the valve is open and the flow of the second fluid through the valve is closed, (3) and a third state where the flow of the first fluid and the second fluid through the valve is open.

In accordance with yet another embodiment, the cartridge may include a first fluid line in fluid communication with the first fluid container and a second fluid line in fluid communication with the second fluid container. A third fluid container may optionally be provided for storing a third fluid therein. The third fluid container may be in fluid communication with at least one of the first fluid line and the second fluid line. In one embodiment, the third fluid may be a disinfectant configured for disinfecting at least one of the first fluid line and the second fluid line.

At least one sterilization device may be in communication with at least one of the first fluid line and the second fluid line. In one embodiment, the sterilization device may be fluid communication with and configured to inject vaporized fluid into at least one of the first fluid line and the second fluid line. In another embodiment, the sterilization device may be configured to irradiate at least a portion of at least one of the first fluid line and the second fluid line, and any fluid contained therein with electromagnetic energy. The electromagnetic energy may be ultraviolet radiation.

In accordance with a further embodiment, the cartridge may include at least one fluid level indicator configured for indicating a volume of at least one of the first fluid inside the first fluid container and the second fluid inside the second fluid container. At least one viewing window may be provided on at least one of the first fluid container or the second fluid container. The at least one viewing window may be configured for providing visual access to an interior of the at least one of the first fluid container and the second fluid container. At least one refilling port may be in fluid communication with at least one of the first fluid container and the second fluid container for refilling the at least at least a portion of at least one of the first fluid container with the first fluid and the second fluid container with the second fluid. In some embodiments, at least a portion of the second fluid container may be received within an interior of the first fluid container, or alternatively at least a portion of the first fluid container may be received within an interior of the second fluid container. At least one sampling chamber may be in fluid communication with and optionally removable from at least one of the first fluid container and the second fluid container. The at least one sampling chamber may be configured to selectively draw a sample of at least the first fluid from the first fluid container and the second fluid from the second fluid container. A power source may be received within the cartridge for providing power to at least one of the at least one pump and the at least one valve. In one embodiment, the first fluid is saline and the second fluid is contrast.

In accordance with a further embodiment, a fluid delivery system is provided where the fluid delivery system may include a cartridge carrier and a cartridge configured for being removably engagable with the cartridge carrier. The cartridge may include a first fluid container configured for storing a first fluid therein and a second fluid container configured for storing a second fluid therein, where the second fluid is different from the first fluid. The cartridge may further include at least one pump configured for delivering under pressure one or both of the first fluid and the second fluid, and at least one valve configured for selectively delivering one or both of the first fluid and the second fluid to the pump. The first and second containers, the at least one pump, and the at least one valve may be received within an outer shell of the cartridge. At least one multi-patient connector may be configured for fluidly connecting the cartridge to a single-patient connector. Engaging the cartridge with the fluid delivery system places various components of the cartridge, such as the first fluid container, the second fluid container, the at least one pump, and/or the at least one valve, in fluid communication with the fluid delivery system, the at least one multi-patient connector, and/or the single-patient connector.

In accordance with another embodiment, a medical connector assembly may include a multi-patient connector and one or more single-patient connectors removably engagable with the multi-patient connector to establish a fluid path therethrough. Each single-patient connector may include a housing having a proximal end opposite a distal end with a central fluid path extending therebetween, a flange extending around the distal end, and a cap removably engaged to the flange. A sterility-maintaining arrangement may be configured for slidably or otherwise removing the cap from the one or more single-patient connectors without exposing the distal end of the one or more single-patient connectors to contamination.

These and other features and characteristics of the portable fluid delivery system and the connector assembly therefor, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only, and are not intended as a definition of the limits of the disclosure. As used in the specification and the claims, the singular form of "a", "an", and "the" include plural referents unless the context clearly dictates otherwise.

DETAILED DESCRIPTION OF THE DISCLOSURE

Figure 1:
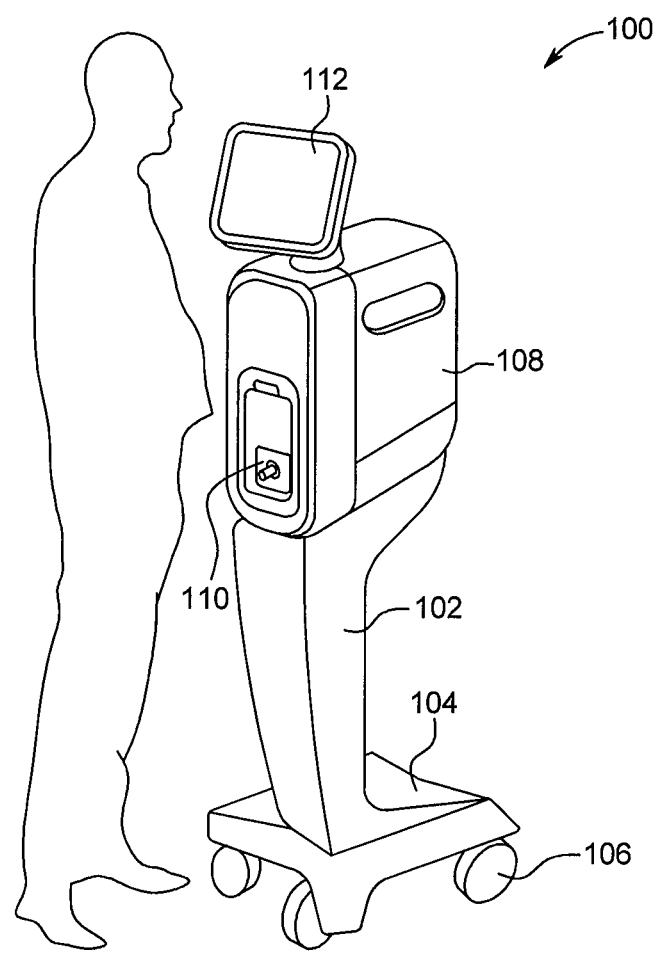
FIG. 1 is a perspective view of a portable fluid delivery system in accordance with one embodiment.

For purposes of the description hereinafter, spatial orientation terms shall relate to the referenced embodiment as it is oriented in the drawing figures. However, it is to be understood that the various embodiments may assume alternative variations and step sequences, except where expressly specified to the contrary. It is also to be understood that the specific devices and processes illustrated in the attached drawings, and described in the following specification, are simply exemplary embodiments. Hence, specific dimensions and other physical characteristics related to the embodiments disclosed herein are not to be considered as limiting.

Referring to the drawings in which like reference characters refer to like parts throughout the several views thereof, the present disclosure is generally directed to a portable fluid delivery system and a connector therefor configured for connection to a fluid path set used in an injection procedure.

Referring initially to FIG. 1, an embodiment of a portable fluid delivery system 100 (hereinafter referred to as "fluid delivery system 100") is shown. The fluid delivery system 100, as described herein, is intended for delivering one or more medical fluids, such as contrast and saline, to a patient as will be readily apparent to those skilled in the medical art. The fluid delivery system 100 includes a frame 102 supported on a base 104. One or more wheels 106 movably support the base 104 and facilitate movement of the fluid delivery system 100 across a floor surface. The fluid delivery system 100 further includes a cartridge carrier 108 connected to the frame 102. In some embodiments, the cartridge carrier 108 removably receives and engages a cartridge having at least one pump, at least one valve, and one or more fluid storage containers for storing medical fluids, as will be described in detail hereinafter. The cartridge carrier 108 includes a connection interface 110 for establishing a fluid connection between the cartridge and a fluid path set 114 (shown in FIG. 3) that delivers fluid from the fluid delivery system 100 to the patient. In some embodiments, the fluid delivery system 100 may include a self-contained power system, such as a battery pack, or it may be connected to an external power source, such as an external power outlet or battery.

With continued reference to FIG. 1, a user interface 112 may be provided to control the operation, receive input from a user, and monitor the performance of the fluid delivery system 100. In one embodiment, the user interface 112 may be in the form of a touch-sensitive display capable of receiving tactile input from the user, may be in the form of a keyboard, or may be designed to receive voice command input. The input from the user may be in the form of an operational command or a status inquiry. For example, the user interface 112 may be used to define the desired injection protocol, including at least one of the injection volume, pressure, and duration. One of ordinary skill in the art will understand that the user interface 112 may be embodied as any type of a control console capable of controlling the operation and monitoring the performance of the fluid delivery system 100.

Figure 2:
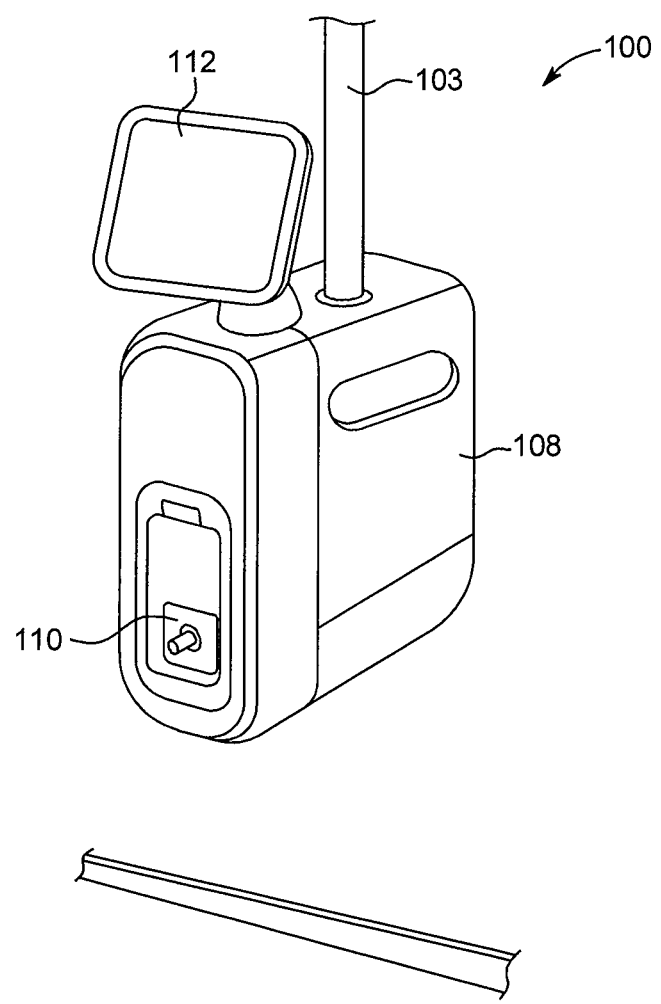
FIG. 2 is a perspective view of a portable fluid delivery system in accordance with another embodiment.

With reference to FIG. 2, an alternative embodiment of the fluid delivery system 100 is shown. Rather than being attached to a movable base 104, as the embodiment shown in FIG. 1, the embodiment in FIG. 2 includes a frame 103 that is fixedly mounted. For example, the frame 103 shown in FIG. 2 may be mounted to the wall, floor, table, or the ceiling of a room. The remaining components of the fluid delivery system 100 shown in FIG. 2, including the cartridge carrier 108, connection interface 110, and the user interface 112, are substantially identical to the components discussed above with reference to FIG. 1.

Figure 3:
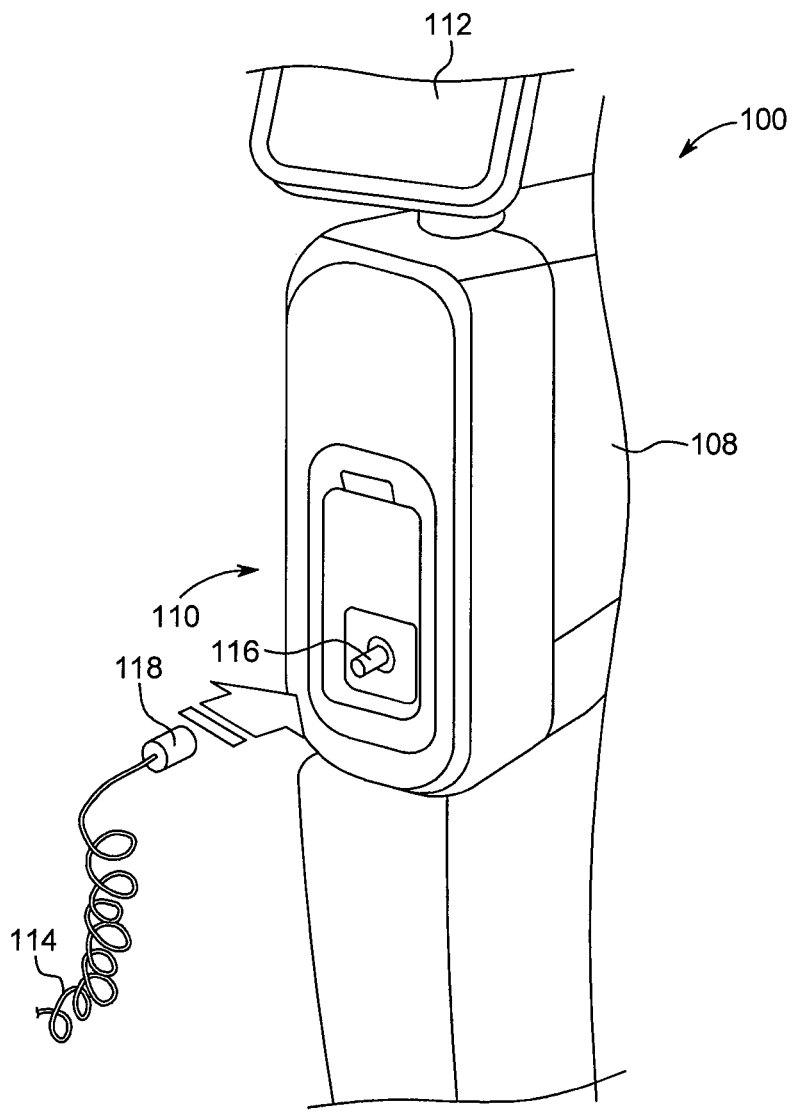
FIG. 3 is a detailed perspective view of a connection interface of the portable fluid delivery system shown in FIG. 1.

Referring to FIG. 3, a detailed view of the connection interface 110 is illustrated. The connection interface 110 is configured for fluidly connecting the fluid delivery system 100 to the fluid path set 114, such as a catheter, a pressure tube, or a connector tube, for delivering one or more fluids from the fluid delivery system 100 to the patient. Desirably, the fluid path set 114 is configured to be discarded after a single use. In one embodiment, the connection interface 110 may include a multi-patient connector 116 in the form of a male connector on the fluid delivery system 100 and a corresponding single-patient connector 118 in the form of a female connector on the fluid path set 114. Alternatively, the multi-patient connector 116 may be in the form of a female connector and the single-patient connector 118 may be in the form of a male connector. In some embodiments, as will be described hereinafter, the multi-patient connector 116 is a multi-patient connector such that it can be used with multiple single-patient fluid path sets 114. The multi-patient connector 116 and the single-patient connector 118 may be embodied as any type of a mechanical connector known in the medical arts. Various non-limiting embodiments of the connectors will be described hereinafter with reference to FIGS. 8A-22C.

Figure 4:
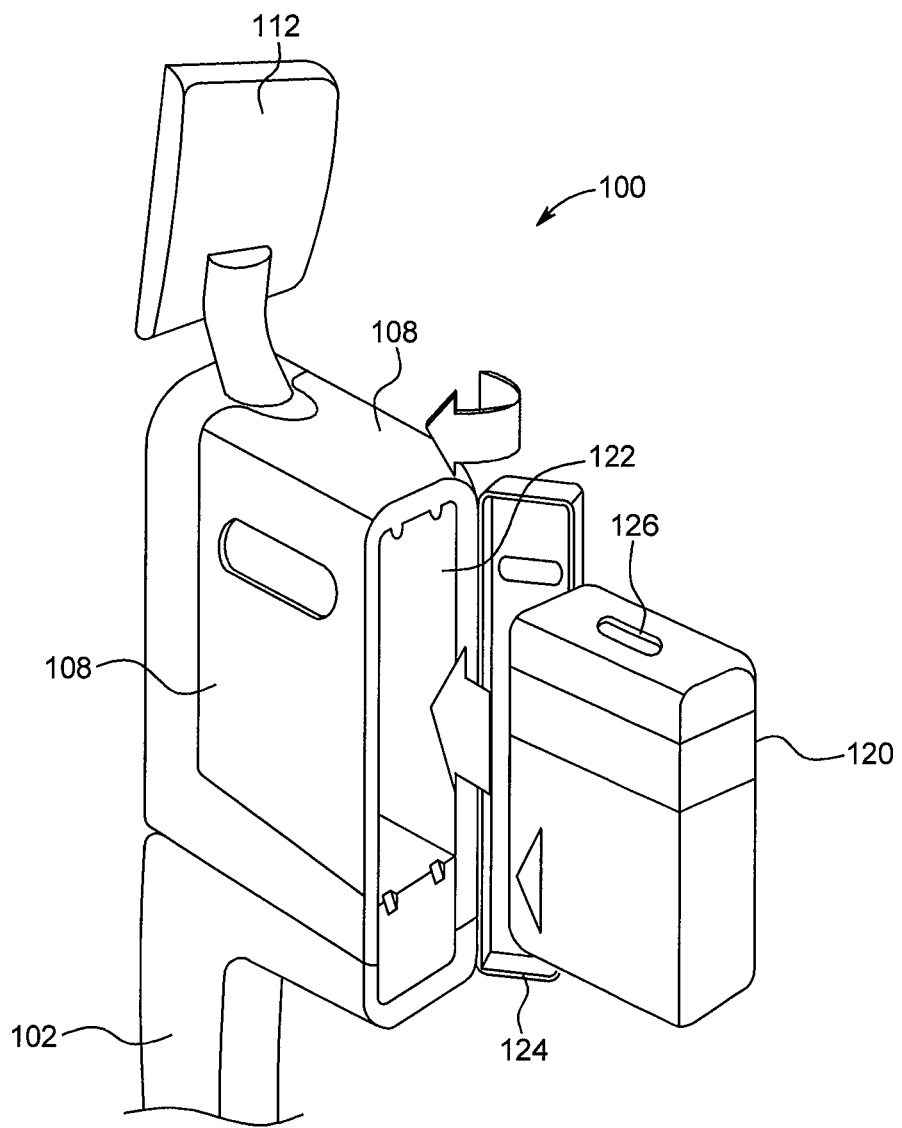
FIG. 4 is a perspective view of a cartridge being loaded into to the portable fluid delivery system shown in FIG. 1.

Referring to FIG. 4, a cartridge 120 having one or more fluid storage containers is removably insertable into and engagable with the cartridge carrier 108. The cartridge 120 is removable from the cartridge carrier 108 so that the cartridge 120 may be replaced after the one or more medical fluids stored within the cartridge 120 are depleted. At least a portion of the cartridge 120 has a rigid sidewall that is dimensionally stable to protect the cartridge 120 and its contents. The cartridge carrier 108 defines an interior compartment 122 configured for receiving the cartridge 120. At least a portion of the cartridge 120, such as the portion of the cartridge 120 proximate to the connection interface 110, may be exposed to facilitate connection with the single patient fluid path set 114 (shown in FIG. 3). A door 124 is secured to the cartridge carrier 108 for enclosing the interior compartment 122 after the cartridge 120 is inserted therein. The interior compartment 122 may be dimensioned such that the cartridge 120 may be inserted in only one direction in order to prevent erroneous insertion of the cartridge 120 into the interior compartment 122. In another embodiment, the cartridge 120 may be secured directly to the frame 102 shown in FIG. 1 or frame 103 shown in FIG. 2.

Figure 5:
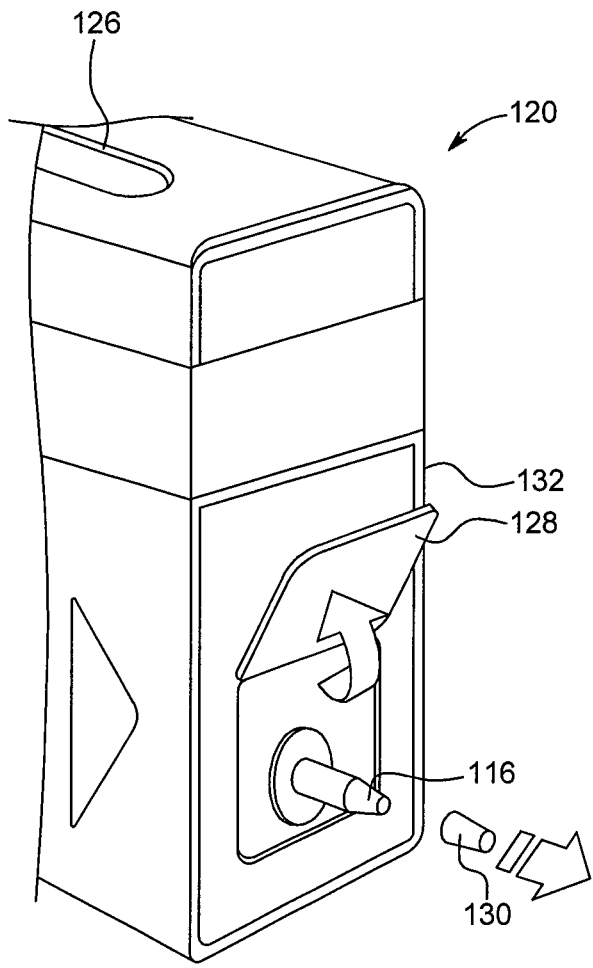
FIG. 5 is a detailed view of connection interface of the cartridge.

As shown in FIG. 5, the cartridge 120 includes a handle 126 to facilitate the carrying of the cartridge 120 and insertion thereof into the interior compartment 122 of the cartridge carrier 108 or placement on the frame 102 or frame 103. The cartridge 120 may further include a flap 128 that covers at least a portion of the multi-patient connector 116 when the cartridge 120 is not in use. For example, the flap 128 may be movable between an open orientation where the multi-patient connector 116 is exposed and a closed configuration where the multi-patient connector 116 is concealed. In some embodiments, the flap 128 may be removed from the cartridge 120 prior to the initial use of the cartridge 120. In other embodiments, the flap 128 may have a breakable membrane that is pierced or otherwise broken prior to the initial use of the cartridge 120. The multi-patient connector 116 may include a cover or cap 130 that covers the multi-patient connector 116 prior to the initial use. The cover 130 is removed prior to connecting the multi-patient connector 116 and the single-patient connector 118 of the fluid path set 114 (shown in FIG. 3), for example, after insertion of cartridge 120 into interior compartment 122.

Figure 6A:
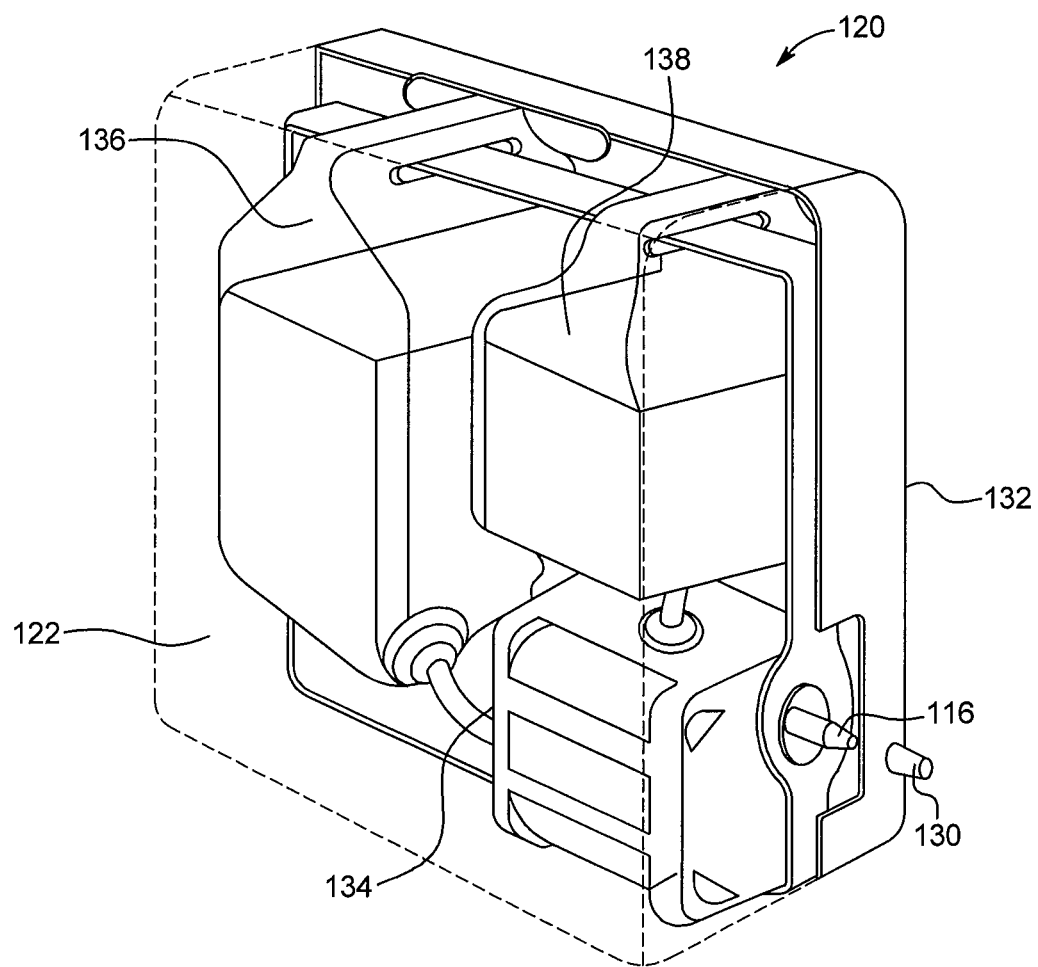
FIG. 6A is a partial transparent view of an arrangement of first and second fluid containers within the cartridge in accordance with a first embodiment.

With reference to FIG. 6A, a partial transparent view of the cartridge 120 is illustrated in accordance with a first embodiment. The cartridge 120 includes an outer shell 132 that defines an outer shape of the cartridge 120. The outer shell 132 defines a hollow interior volume that receives a pump 134, such as a high-pressure peristaltic pump and one or more fluid containers. A power source 156, such as a battery (shown in FIG. 6B), may be provided within the outer shell 132 of the cartridge 120 for powering the at least one pump 134 and/or the at least one valve 140 (shown in FIG. 6B). In some embodiments, the at least one pump 134 and/or the at least one valve may be provided externally from the outer shell 132 of the cartridge 120. In the embodiment shown in FIG. 6A, the cartridge 120 includes a first fluid container 136 for receiving a first fluid, such as saline, and a second fluid container 138 for receiving a second fluid, such as contrast. One or both of the first and second fluid containers 136, 138 may be refillable or disposable containers. In some embodiments, at least one of the first and second fluid containers 136, 138 may have a refilling port (shown in FIG. 6B) for refilling the contents of the first and second fluid containers 136, 138 once at least a portion of the first and second fluids has been depleted therefrom. The cartridge 120 may further comprise one or more electrical contacts for establishing electrical communication with the user interface 112 and/or other components of the fluid delivery system 100.

The first and second fluid containers 136, 138 may have the same or different shapes and/or volumes. In some embodiments, the first and second fluid containers 136, 138 may have a flexible sidewall. For example, at least one of the first and second fluid containers 136, 138 may have a collapsible structure, such as a bellows arrangement, that collapses as fluid is delivered from the first and/or second fluid containers 136, 138. In this manner, the void left by the fluid delivered from the first and/or second fluid containers 136, 138 does not have to be replaced with air to prevent a vacuum from being formed within the first and/or second fluid containers 136, 138. In other embodiments, the first and second fluid containers 136, 138 may have rigid sidewalls. The first and second fluid containers 136, 138 may be made from any medical-grade material, such as medical-grade plastic. The first and second fluid containers 136, 138 are secured within the hollow interior volume of the outer shell 132 of the cartridge 120 to prevent movement of the first and second fluid containers 136, 138 within the cartridge 120. The first and second fluid containers 136, 138 may be permanently or removably connected to the cartridge 120. In one embodiment, the first and second fluid containers 136, 138 are removably connected to the cartridge 120 such that one or both of first and second fluid containers 136, 138 may be replaced and the cartridge 120 and other components thereof can be reused. In another embodiment, the first and second fluid containers are permanently connected within the cartridge 120 such that the entire cartridge 120, along with the first and second containers 136, 138, must be replaced after use. In specific embodiments, the at least on pump 134 may be removable from cartridge 120 and may be used in additional cartridges after disposal of the first cartridge. In an embodiment where the first and second fluid containers 136, 138 are refillable, the cartridge 120 may be reused after refilling at least one of the first and second containers 136, 138. In other embodiments, more than two fluid containers may be provided within the hollow interior volume of the cartridge 120.

Figure 6B:
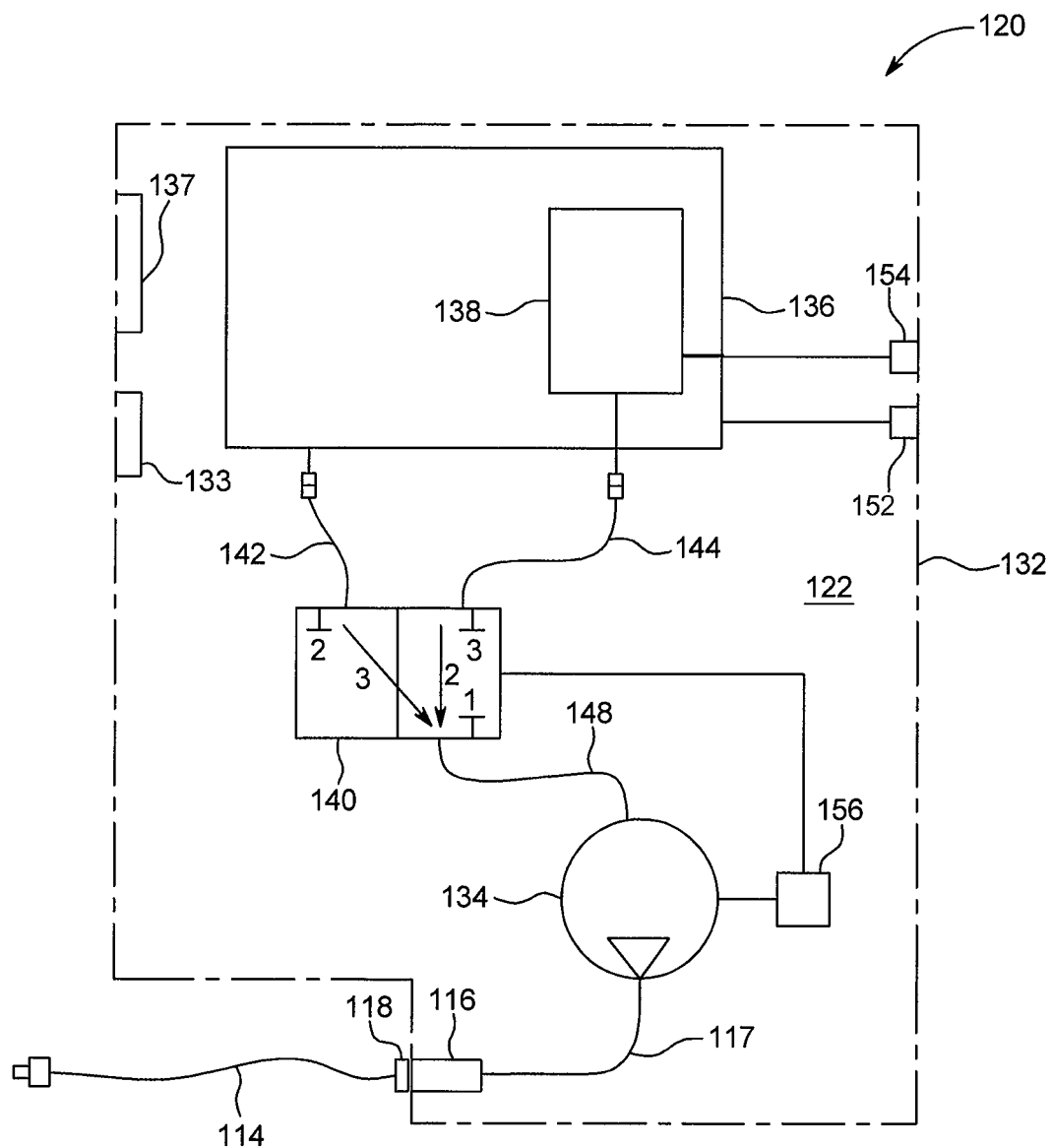
FIG. 6B is a schematic representation of an arrangement of first and second fluid containers within the cartridge in accordance with a second embodiment.

With reference to FIG. 6B, a schematic representation of the cartridge 120 is illustrated in accordance with a second embodiment. The cartridge 120 includes an outer shell 132 that defines an outer shape of the cartridge 120. The outer shell 132 defines a hollow interior compartment 122 that receives one or more fluid containers. In the embodiment shown in FIG. 6B, the cartridge 120 includes a first fluid container 136 for receiving a first fluid, such as saline, and a second fluid container 138 for receiving a second fluid, such as contrast. One or both of the first and second fluid containers 136, 138 may be refillable containers, or they may be disposable containers. For example, first and second refilling ports 152, 154 may be provided for refilling the contents of the first and second fluid containers 136, 138 once at least a portion of the first and second fluids has been depleted therefrom.

The second fluid container 138 may be received within at least a portion of the first fluid container 136. In one embodiment, the second fluid container 138 is received entirely within the first fluid container 136. In some embodiments, the first and second fluid containers 136, 138 may have a flexible sidewall. In other embodiments, the first and second fluid containers 136, 138 may have rigid sidewalls. In embodiments where the second container 138 is constructed from a material that allows gas and water vapor transmission from the interior of the second container 138 to the exterior thereof, the rate of gas and water vapor transmission can be reduced by surrounding the second container 138 with the first fluid within the first fluid container 136 instead of air. One or both of the first and second fluid containers 136, 138 are secured within the hollow interior compartment 122 of the outer shell 132 of the cartridge 120 to prevent the movement of the first and/or second fluid containers 136, 138 within the cartridge 120. In one embodiment, the first fluid container 136 may be removably connected to the cartridge 120 such that the first fluid container 136, and the second fluid container 138 received therein, may be replaced. In one embodiment, the first fluid container 136 and/or the second fluid container 138 may be removably connected to the cartridge 120 such that the first fluid container 136 and/or the second fluid container 138 may be replaced. In another embodiment, the first container 136 is permanently connected within the cartridge 120 such that the entire cartridge 120 must be replaced after use. In an embodiment where the first and second fluid containers 136, 138 are refillable, the cartridge 120 may be reused after refilling at least one of the first and second containers 136, 138. In other embodiments, more than two fluid containers may be provided within the hollow interior volume of the cartridge 120 and, in certain embodiments, more than one fluid container may be contained within the first and/or the second fluid containers 136, 138. The first and second fluid containers 136, 138 are connected to a valve 140 (shown in FIGS. 7A-7H) that delivers at least one of the first and second fluids from the first and second containers 136, 138 to at least one pump 134, as will be described hereinafter. The first and second fluid containers 136, 138 are connected to the valve 140 (shown in FIGS. 7A-7H) via first and second fluid lines 142, 144, respectively.

With continued reference to FIG. 6B, a viewing port 133 may be provided on the outer shell 132 of the cartridge 120. The viewing port 133 may be configured to provide a visual indication of a condition of the first and/or second fluid in the first and second fluid containers 136, 138. For example, the viewing port 133 may provide a visual indication of the fluid level within the first and/or second fluid containers 136, 138. Further, in embodiments where the second fluid is contrast, the viewing port 133 allows a visual verification of crystallinity of the contrast. One or both of the first and second fluid containers 136, 138 may have the viewing port 133. The viewing port 133 may be aligned with a corresponding viewing port on an exterior of cartridge carrier 108.

With continued reference to FIG. 6B, the cartridge 120 may have a level indicator 137. In some embodiments, the level indicator 137 may be in the form of indicia on the viewing window 133 to provide a visual indication of the volume of the first and/or second fluid inside the first and second fluid containers 136, 138. In other embodiments, the level indicator 137 may be an electronic sensor, such as an optical, ultrasound, or a weight sensor, configured to measure the volume of the first and/or second fluid inside the first and second fluid containers 136, 138. The output from the level indicator 137 may be visually displayed on the user interface 112.

According to certain embodiments, a power source 156, such as a battery or rechargeable battery, may be provided within the outer shell 132 of the cartridge 120 for powering the pump 134 and/or the valve 140. The power source 156 may also be provided externally, such as by a power cord connection to an external power source.

Figure 7A:
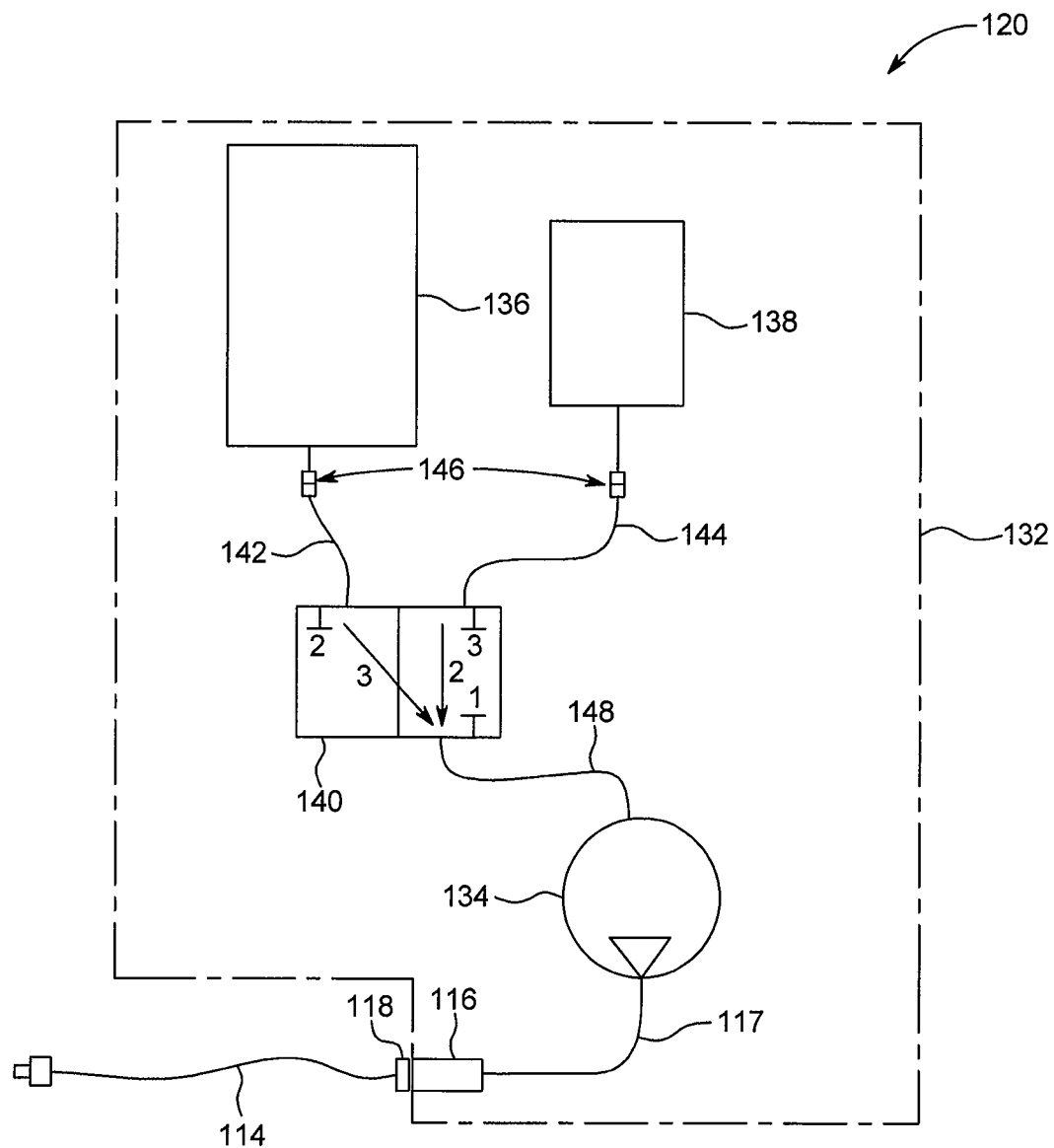
FIG. 7A is a schematic representation of the cartridge in accordance with a one embodiment.

Referring to FIG. 7A, a schematic diagram of the cartridge 120 is illustrated in accordance with an embodiment. First and second fluids are delivered from the first and second fluid containers 136, 138 to the valve 140 via first and second fluid lines 142, 144, respectively. Each of the first and second fluid containers 136, 138 may include a connector 146 for connecting the first and second containers 136, 138 to the first and second fluid lines 142, 144, respectively. In some embodiments, the connector 146 may comprise a one-way valve to prevent the flow of fluid from the first and second fluid lines back to the first and second fluid containers 136, 138. In other embodiments, the connector 146 may be an aseptic connector configured to prevent contamination of the first and second fluids flowing from the first and second containers 136, 138 through the first and second fluid lines 142, 144. In yet another embodiment, the connector 146 may be a combination of a one-way valve with aseptic features. Connectors 146 may allow for removal and replacement of the first and/or second containers 136, 138. In a further embodiment, the first and second fluid containers 136, 138 are directly connected to the valve 140.

With continuing reference to FIG. 7A, the valve 140 may be a multi-position valve that is connected to a third fluid line 148. The valve 140 may be configured to receive first and second fluids from the first and second fluid containers 136, 138 through the first and second fluid lines 142, 144, respectively. In another embodiment, the valve 140 may be configured to receive first and second fluids directly from the first and second fluid containers 136, 138. Depending on the position of the valve 140, the supply of the first and second fluids may be open or closed such that only one of the first or second fluids or both of the first and second fluids can flow through the valve 140. For example, the valve 140 may have three positions/states: (1) the flow of first and second fluids received from the first and second fluid containers 136, 138 is closed; (2) the flow of the first fluid received from the first fluid container 136 is open, while the flow of the second fluid received from the second fluid container 138 is closed; and (3) the flow of the second fluid received from the second fluid container 138 is open, while the flow of the first fluid received from the first fluid container 136 is closed. Alternatively, the valve 140 may have three positions/states as follows: (1) the flow of first and second fluids received from the first and second fluid containers 136, 138 is closed; (2) the flow of the second fluid received from the second fluid container 138 is open, while the flow of the first fluid received from the first fluid container 136 is closed; and (3) the flow of the second fluid received from the second fluid container 138 is open, while the flow of the first fluid received from the first fluid container 136 is closed. The valve 140 may optionally include a fourth state where the flow of the first fluid received from the first fluid container 136 and the flow of the second fluid from the second fluid container 138 are open. The valve 140 may be electronically controlled to switch between the three positions/states through the user interface 112 or it may be manually actuated.

With continued reference to FIG. 7A, the first fluid or the second fluid flows from the valve 140 to the pump 134 through the third fluid line 148. In another embodiment, the valve 140 is connected directly to the pump 134. In one embodiment, the valve 140 may be formed integrally with the pump 134. In some embodiments, the pump 134 may be a high pressure peristaltic pump having an input configured for receiving at least one of or both of the first and second fluids and an output for delivering a quantity of the first and/or second fluid under pressure. In another embodiment, the pump 134 is electronically controlled through the user interface 112. Depending on the performance requirements, alternate pump designs may be used. For example, the pump may be, without limitation, one or more of the following: a piston pump, a syringe-based pump, a diaphragm pump, a rotary pump, a screw pump, a gear pump, and a vane pump. An outlet of the pump 134 may be connected to the multi-patient connector 116 by way of a fluid outlet line 117.

Figure 7B:
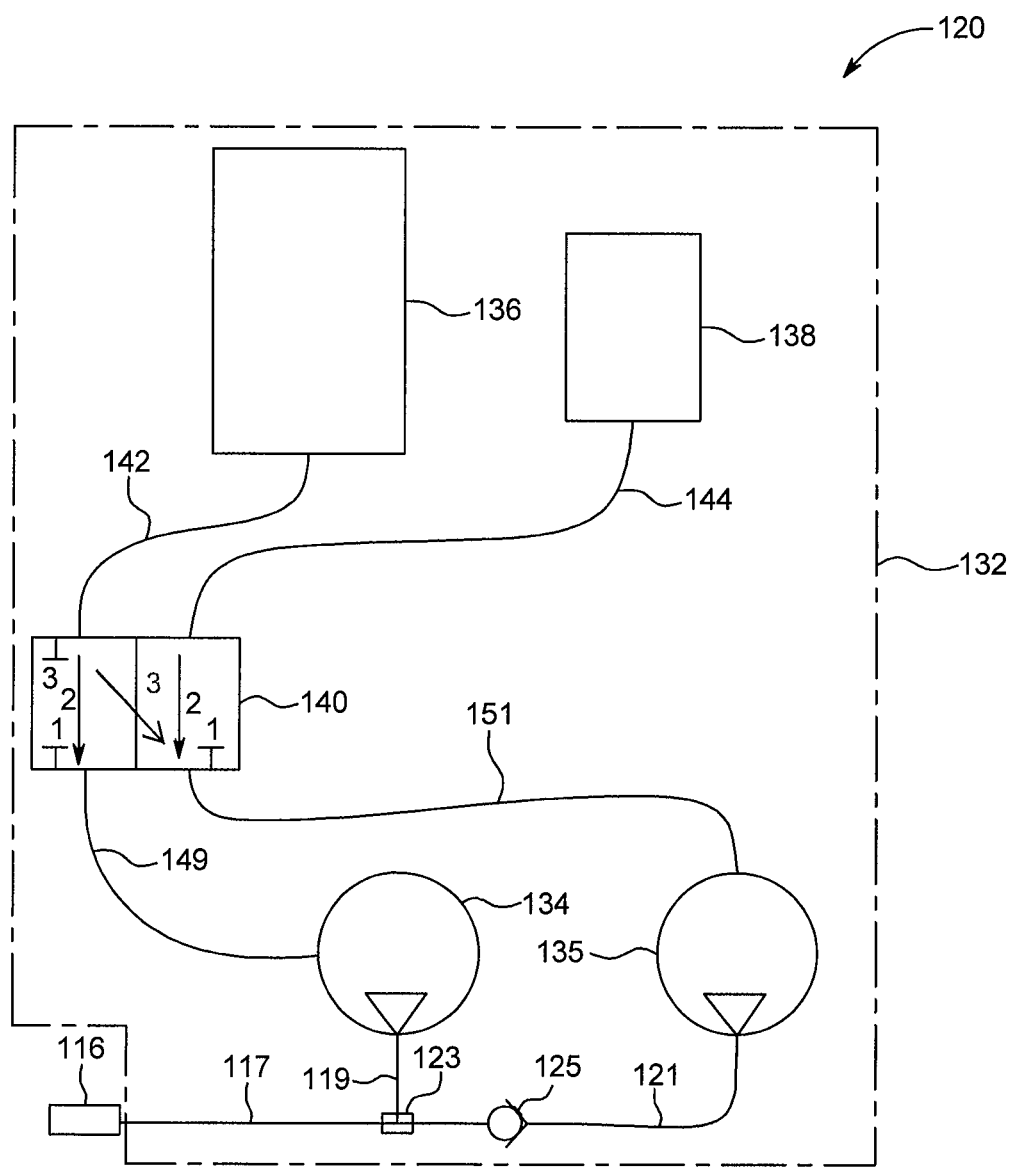
FIG. 7B is a schematic representation of the cartridge in accordance with another embodiment.

With reference to FIG. 7B, a schematic diagram of the cartridge 120 is illustrated in accordance with another embodiment. First and second fluids are delivered from the first and second fluid containers 136, 138 to the valve 140 via first and second fluid lines 142, 144, respectively. The valve 140 is a multi-position valve that may be connected to a first outlet line 149 and a second outlet line 151. In one embodiment, the first fluid flows from the first fluid container 136 through the first fluid line 142, through the valve 140 and through the first outlet line 149. The second fluid flows from the second fluid container 138 through the second fluid line 144, through the valve 140 and through the first and/or second outlet line 149, 151. Depending on the position of the valve 140, the supply of the first and second fluids may be open or closed such that only one of or both of the first and second fluids can flow through the valve 140. For example, the valve 140 may have three positions/states: (1) the flow of first and second fluids received from the first and second fluid containers 136, 138 is closed; (2) the flow of the first fluid received from the first fluid container 136 is open to allow the first fluid to flow through the second outlet line 151, while the flow of the second fluid received from the second fluid container 138 is closed; and (3) the flow of the first and second fluids received from the first and second fluid containers 136, 138 is open to allow the first and second fluids to flow through the first and second outlet lines 149, 151. The valve 140 may be electronically controlled to switch between the three positions/states through the user interface 112 or it may be manually actuated.

With continued reference to FIG. 7B, the first fluid and the second fluid flow from the valve 140 to a first pump 134 and a second pump 135 through the first and second fluid outlet lines 149, 151, respectively. In another embodiment, the valve 140 is connected directly to the first and second pumps 134, 135. Outlets of the first and second pumps 134, 135 are connected to the multi-patient connector 116 by way of a first and second pump outlet lines 119, 121. The first and second pump outlet lines 119, 121 may be joined together to a single fluid outlet line 117 at a connector 123. A one-way check valve 125 is provided on the second pump outlet line 121 to prevent the first fluid from flowing into the second pump 135, or the second fluid container 138 and contaminating the second fluid. In one embodiment, the connector 123 and the check valve 125 may be integrated into a unitary structure.

Figure 7C:
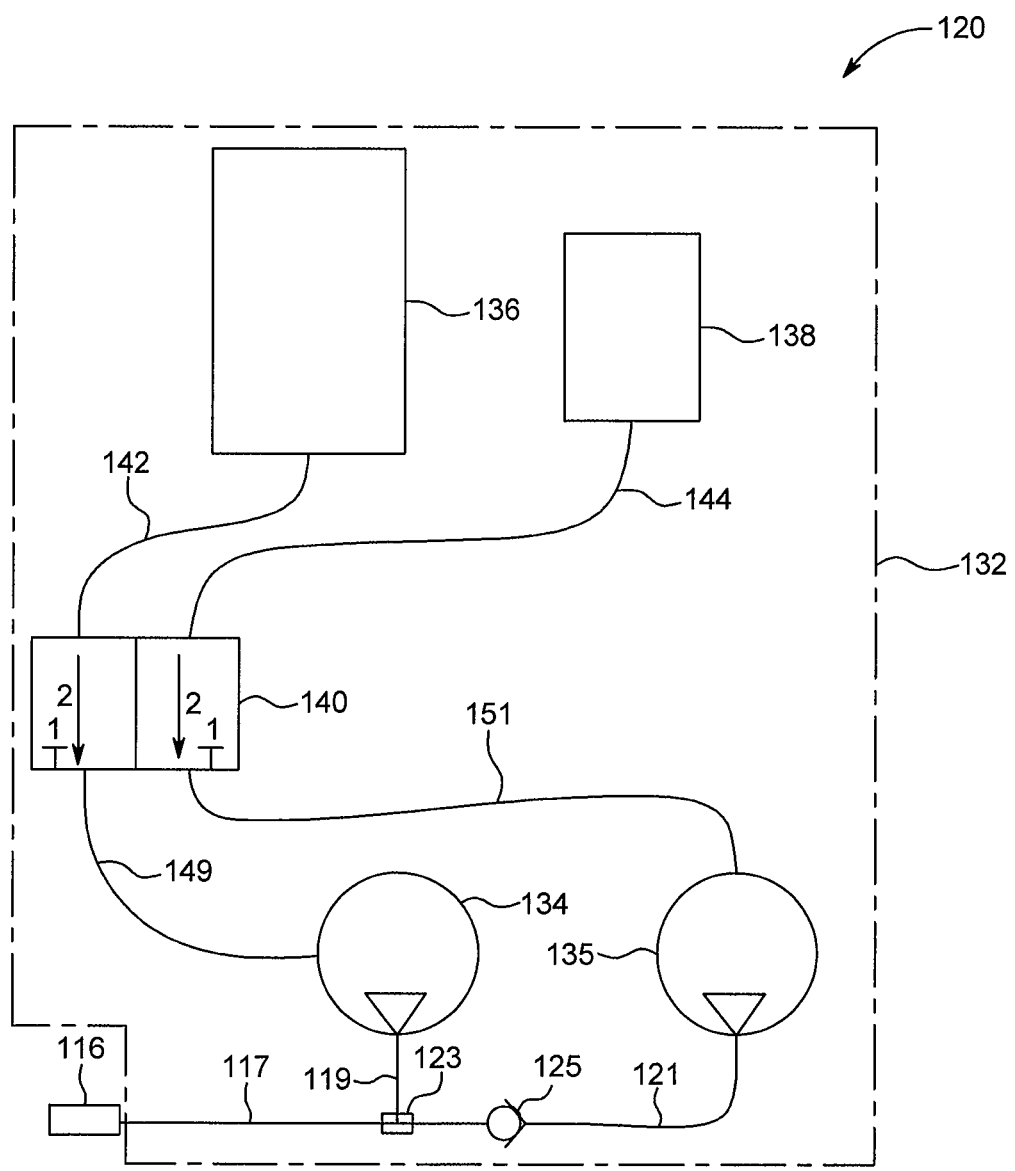
FIG. 7C is a schematic representation of the cartridge in accordance with another embodiment.

With reference to FIG. 7C, a schematic diagram of the cartridge 120 is illustrated in accordance with another embodiment. First and second fluids are delivered from the first and second fluid containers 136, 138 to the valve 140 via first and second fluid lines 142, 144, respectively. The valve 140 is a multi-position valve that is connected to a first outlet line 149 and a second outlet line 151. In one embodiment, the first fluid flows from the first fluid container 136 through the first fluid line 142, through the valve 140 and through the first outlet line 149. The second fluid flows from the second fluid container 138 through the second fluid line 144, through the valve 140 and through the second outlet line 151. Depending on the position of the valve 140, the supply of the first and second fluids may be open or closed such that both or neither of the first and second fluids can flow through the valve 140. For example, the valve 140 may have two positions/states: (1) the flow of first and second fluids received from the first and second fluid containers 136, 138 is closed; and (2) the flow of the first and second fluids received from the first and second fluid containers 136, 138 is open to allow the first and second fluids to flow through the first and second outlet lines 149, 151, respectively. The valve 140 may be electronically controlled to switch between the two positions/states through the user interface 112 or it may be manually actuated. Two separate valves 140 can be provided for each of the first and second fluid lines 142, 144.

With continued reference to FIG. 7C, the first fluid and the second fluid flow from the valve 140 to a first pump 134 and a second pump 135 through the first and second fluid outlet lines 149, 151, respectively. In another embodiment, the valve 140 is connected directly to the first and second pumps 134, 135. Outlets of the first and second pumps 134, 135 are connected to the multi-patient connector 116 by way of a first and second pump outlet lines 119, 121. The first and second pump outlet lines 119, 121 may be joined together to a single fluid outlet line 117 at a connector 123. A one-way check valve 125 is provided on the second pump outlet line 121 to prevent the first fluid from flowing into the second pump 135 or the second fluid container 138 and contaminating the second fluid. In one embodiment, the connector 123 and the check valve 125 may be integrated into a unitary structure.

Figure 7D:
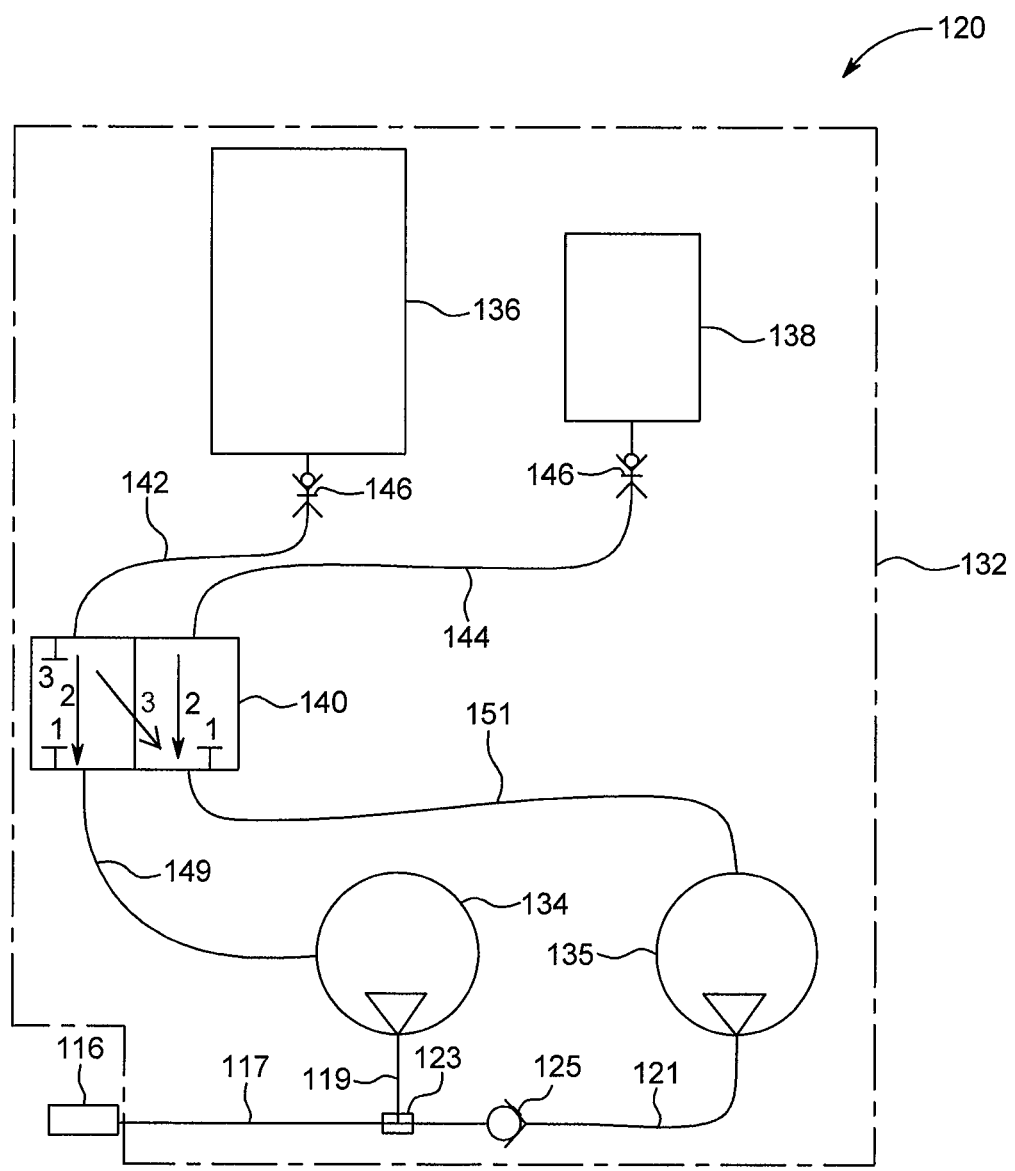
FIG. 7D is a schematic representation of the cartridge in accordance with another embodiment.

With reference to FIG. 7D, a schematic diagram of the cartridge 120 is illustrated in accordance with an additional embodiment. First and second fluids are delivered from the first and second fluid containers 136, 138 to the valve 140 via first and second fluid lines 142, 144, respectively. Each of the first and second fluid containers 136, 138 may include a connector 146 for connecting the first and second containers 136, 138 to the first and second fluid lines 142, 144, respectively. In some embodiments, the connector 146 may be a one-way valve to prevent the flow of fluid from the first and second fluid lines 142, 144 back to the first and second fluid containers 136, 138. In other embodiments, the connector 146 may be an aseptic connector configured to prevent contamination of the first and second fluids flowing from the first and second containers 136, 138 through the first and second fluid lines 142, 144. In yet another embodiment, the connector 146 may be a combination of a one-way valve with aseptic features. The valve 140 is a multi-position valve that is connected to a first outlet line 149 and a second outlet line 151. In one embodiment, the first fluid flows from the first fluid container 136 through the first fluid line 142, through the valve 140 and through the first or second outlet line 149, 151. The second fluid flows from the second fluid container 138 through the second fluid line 144, through the valve 140 and through the second outlet line 151. Depending on the position of the valve 140, the supply of the first and second fluids may be open or closed such that only one or both of the first and second fluids can flow through the valve 140. For example, the valve 140 may have three positions/ states: (1) the flow of first and second fluids received from the first and second fluid containers 136, 138 is closed; (2) the flow of the first fluid received from the first fluid container 136 is open to allow the first fluid to flow through the first outlet line 149, while the flow of the second fluid received from the second fluid container 138 is open to allow the second fluid to flow through the second outlet line 151; and (3) the flow of the first fluids received from the first fluid container 136 is open to allow the first a fluid to flow through the second outlet line 151. The valve 140 may be electronically controlled to switch between the three positions/states through the user interface 112 or it may be manually actuated.

With continued reference to FIG. 7D, the first fluid and the second fluid flow from the valve 140 to a first pump 134 and a second pump 135 through the first and second fluid outlet lines 149, 151. In another embodiment, the valve 140 is connected directly to the first and second pumps 134, 135. Outlets of the first and second pumps 134, 135 are connected to the multi-patient connector 116 by way of a first and second pump outlet lines 119, 121. The first and second pump outlet lines 119, 121 may be joined together to a single fluid outlet line 117 at a connector 123. A one-way check valve 125 may be provided in the second pump outlet line 121 to prevent the first fluid from flowing into the second pump 135 or the second fluid container 138 and contaminating the second fluid in the pump 135 or in fluid line 151. In one embodiment, the connector 123 and the check valve 125 may be integrated into a unitary structure.

Figure 7E:
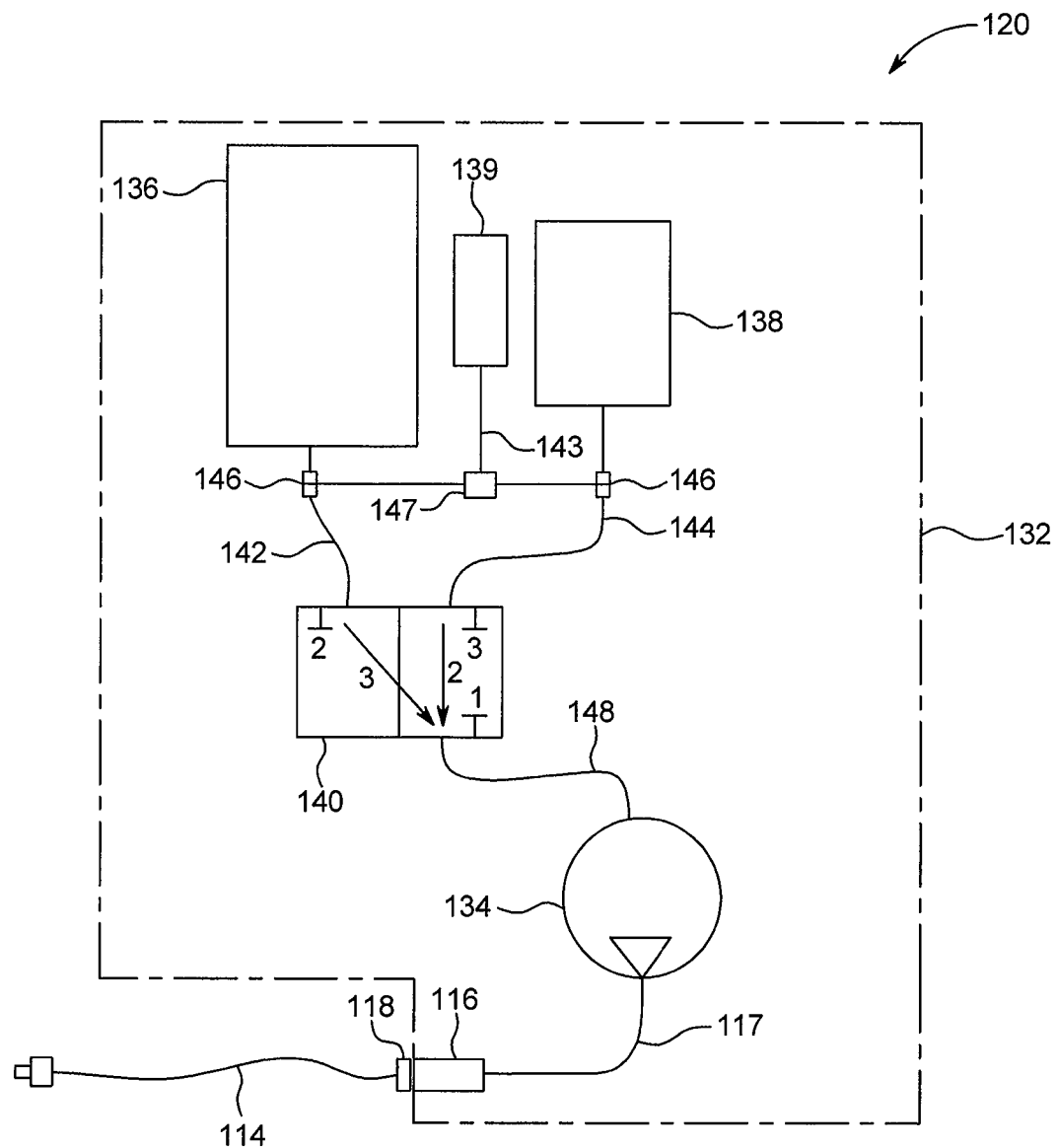
FIG. 7E is a schematic representation of the cartridge in accordance with another embodiment.

With reference to FIG. 7E, a schematic diagram of the cartridge 120 is illustrated in accordance with a further embodiment. First and second fluids are delivered from the first and second fluid containers 136, 138 to the valve 140 via first and second fluid lines 142, 144, as further detailed hereinabove. One or both of the first and second fluid containers 136, 138 may include a connector 146 for connecting the first and second fluid containers 136, 138 to the first and second fluid lines 142, 144, respectively. In some embodiments, the connector 146 may be a one-way valve to prevent the flow of fluid from the first and second fluid lines back to the first and second fluid containers 136, 138. In other embodiments, the connector 146 may be an aseptic connector configured to prevent contamination of the first and second fluids flowing from the first and second fluid containers 136, 138 through the first and second fluid lines 142, 144. In yet another embodiment, the connector 146 may be a combination of a one-way valve with aseptic features.

With further reference to FIG. 7E, a third fluid is selectively delivered from a third container 139 to one of or both of the first and second fluid lines 142, 144 via a third fluid line 143. The third fluid line 143 may include a connector 147 configured to selectively deliver the third fluid form the third fluid container 139 to one or both of the first and second fluid lines 142, 144. In one embodiment, the third fluid line 143 connects directly to the connector 147 on the first and second fluid lines 142, 144. In another embodiment, the third fluid line 143 connects directly to the first and second fluid lines 142, 144. In a further embodiment, each of the first and second fluid lines 142, 144 may be in fluid communication with a separate container having a third and fourth fluid (not shown). Connector 147 may also include a valve that may be operated by either manually or via interface 112 to open fluid communication from the third container to one of or both of the first and second fluid lines 142, 144 via a third fluid line 143.

With continued reference to FIG. 7E, the third fluid container 139 may contain a third fluid that is a disinfecting or sterilizing fluid. Once the third fluid passes through one or both of the first and second fluid lines 142, 144, the third fluid disinfects or sterilizes the fluid line through which it flows. In this manner, the fluid path between the first and/or second fluid containers 136, 138 and the multi-patient connector 116 can be disinfected and/or sterilized. The cleaning/ sterilization of the fluid path between the first and second fluid containers 142, 144 and the multi-patient connector 116 can be carried out after each injection procedure, or it may be carried out selectively after a number of injection procedures have been completed. While FIG. 7E illustrates the combination of the third fluid container 139 with the valve 140 and pump 134 arrangement as shown in FIG. 7A, it is to be understood that third fluid container 139 may be incorporated into the valve and pump arrangement of any of the embodiments shown in FIGS. 6B and 7B-7H to provide cleaning and/or sterilization capability to all embodiments of the cartridge 120 described herein.

Figure 7F:
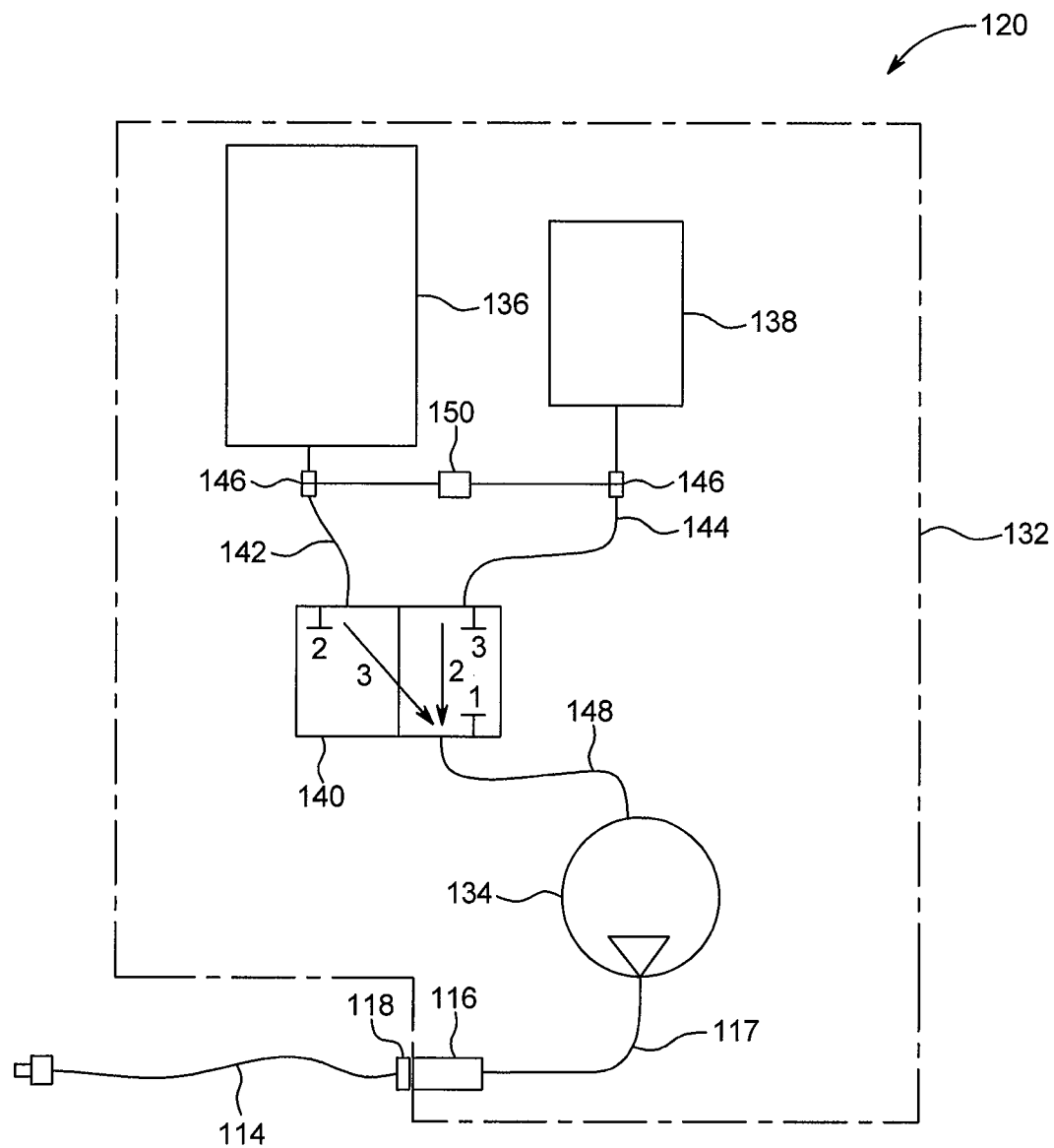
FIG. 7F is a schematic representation of the cartridge in accordance with another embodiment.

With reference to FIG. 7F, a schematic diagram of the cartridge 120 is illustrated in accordance with a further embodiment. First and second fluids are delivered from the first and second fluid containers 136, 138 to the valve 140 via first and second fluid lines 142, 144, as further detailed herein with reference to FIG. 7A. The cartridge 120 may further include at least one sterilization device 150 disposed therein, for example in fluid connection with at least one of the fluid paths between the first and second containers 136, 138 and the multi-patient connector 116. In one embodiment, the sterilization device 150 is disposed between the first and second fluid containers 136, 138 and the valve 140. For example, the sterilization device 150 may be disposed between the first and second fluid containers 136, 138 and the valve 140 such that it acts on one or both of the first and second fluid lines 142, 144. The sterilization device 150 may be configured to inject vaporized fluid into one or both of the first and second fluid lines 142, 144. Once the vaporized fluid, such as water, alcohol, or hydrogen peroxide, passes through one or both of the first and second fluid lines 142, 144, the vaporized fluid disinfects or sterilizes the fluid line through which it flows. In this manner, at least a portion of the fluid path between the first and second fluid containers 136, 138 and the multi-patient connector 116 can be cleaned and sterilized. The cleaning of the fluid path between the first and second fluid containers 136, 138 and the multi-patient connector 116 can be carried out after each injection procedure, or it may be carried out selectively after a number of injection procedures have been completed. While FIG. 7F illustrates the combination of sterilization device 150 with the valve and pump arrangement as shown in FIG. 7A, it is to be understood that the sterilization device 150 may be incorporated into the valve 140 and pump 134 arrangement of any of the embodiments shown in FIGS. 6B and 7B-7H to provide cleaning and/or sterilization capability to all embodiments of the cartridge 120 described herein. Further, while FIG. 7F illustrates the sterilization device 150 provided between the first and second fluid containers 136, 138 and the valve 140, the sterilization device 150 may also be provided in a fluid path between the valve 140 and the multi-patient connector 116. In certain embodiments, one or more sterilization devices 150 may be provided within the cartridge 120.

Figure 7G:
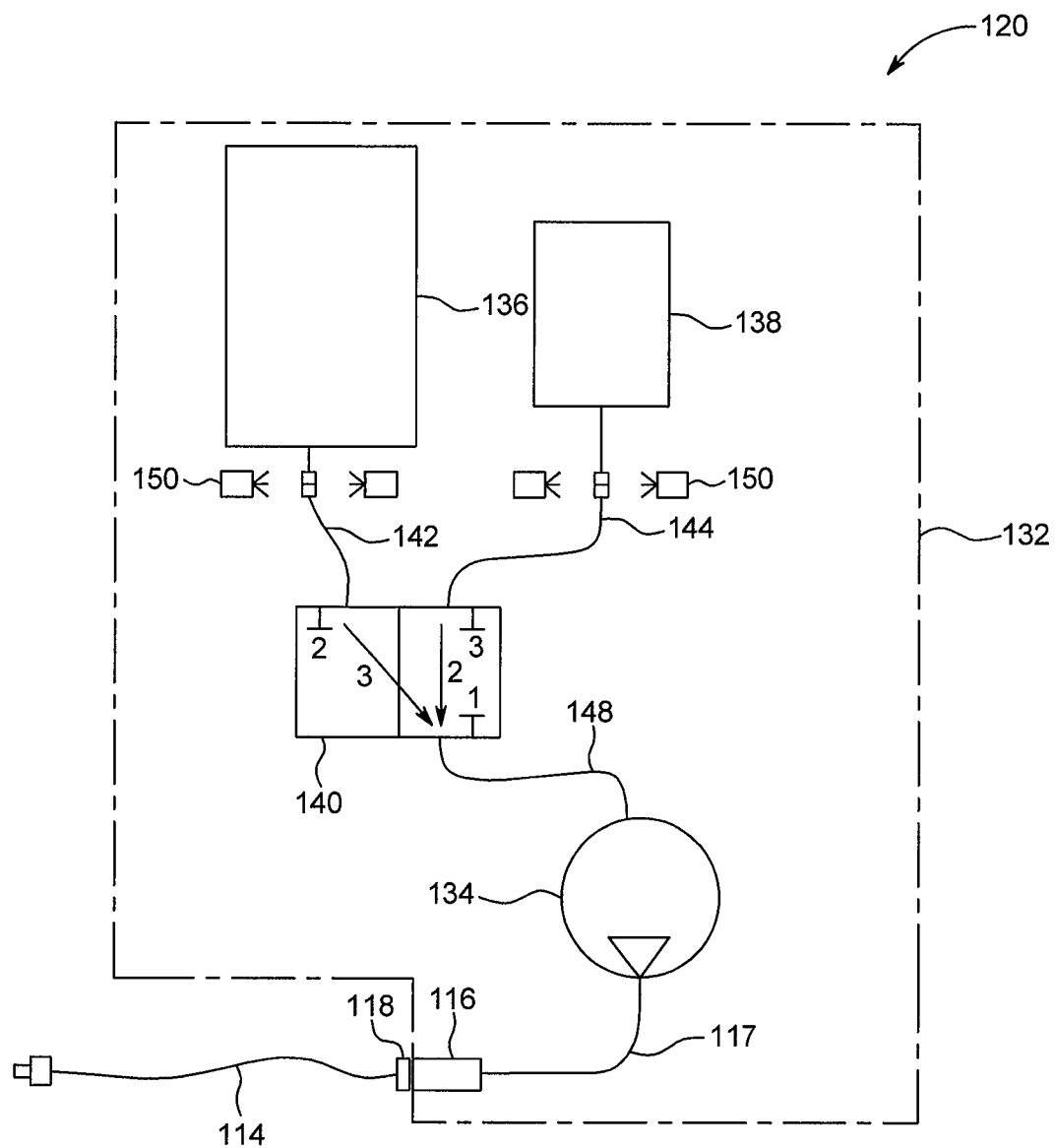
FIG. 7G is a schematic representation of the cartridge in accordance with another embodiment.

With reference to FIG. 7G, a schematic diagram of the cartridge 120 is illustrated in accordance with another embodiment. First and second fluids are delivered from the first and second fluid containers 136, 138 to the valve 140 via first and second fluid lines 142, 144, as further detailed herein with reference to FIG. 7A. The cartridge 120 may further include at least one sterilization device 150 disposed therein, for example in connection with at least one of the fluid paths between the first and second containers 136, 138 and the multi-patient connector 116. In one embodiment, the sterilization device 150 may be disposed between the first and second fluid containers 136, 138 and the valve 140. In another embodiment, the sterilization device 150 may be provided between the valve 140 and the multi-patient connector 116. One or more sterilization devices 150 may be provided within the cartridge 120.

With continued reference to FIG. 7G, the sterilization device 150 may be configured to irradiate at least a portion of the fluid path between the first and second fluid containers 136, 138 and the multi-patient connector 116 with electromagnetic radiation. For example, the sterilization device 150 may be configured to direct ultraviolet light or other high energy radiation onto the fluid path. Once the electromagnetic radiation acts on at least a portion of the fluid path between the first and second fluid containers 136, 138 and the multi-patient connector 116, the portion of the fluid path that is irradiated with electromagnetic radiation is sterilized to prevent contamination of the fluid flowing therethrough. In this manner, at least a portion of the fluid path between the first and second fluid containers 136, 138 and the multi-patient connector 116 can be cleaned and/or sterilized. The cleaning/sterilization of the fluid path between the first and second fluid containers 136, 138 and the multi-patient connector 116 can be carried out after each injection procedure, or it may be carried out selectively after a number of injection procedures have been completed. While FIG. 7G illustrates the combination of sterilization device 150 with the valve and pump arrangement as shown in FIG. 7A, it is to be understood that the sterilization device 150 may be incorporated into the valve 140 and pump 134 arrangement of any of the embodiments shown in FIGS. 6B and 7B-7H to provide cleaning and/or sterilization capability to all embodiments of the cartridge 120 described herein.

Figure 7H:
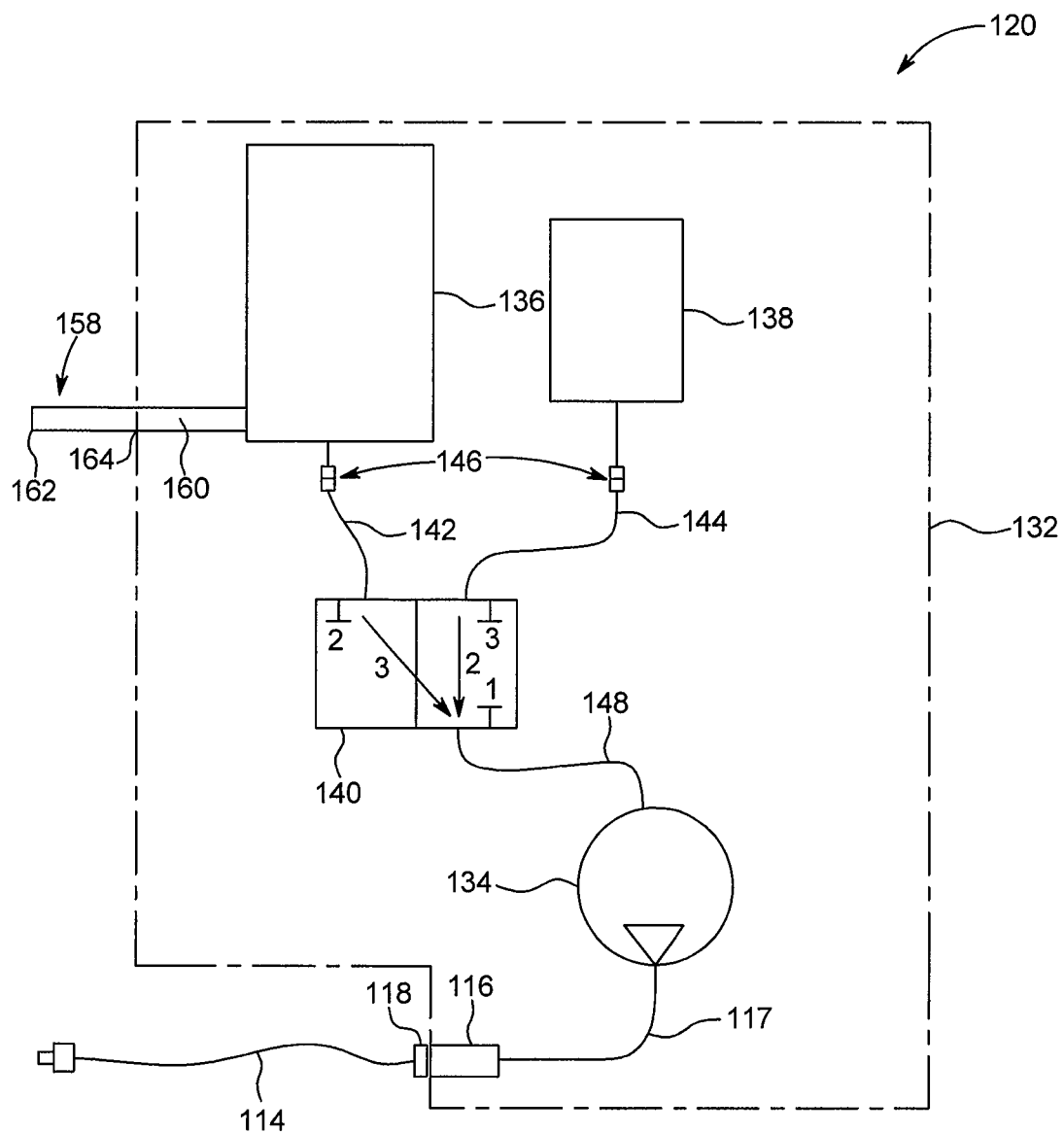
FIG. 7H is a schematic representation of the cartridge in accordance with another embodiment.

With reference to FIG. 7H, a schematic diagram of the cartridge 120 is illustrated in accordance with another embodiment. In the embodiment shown in FIG. 7H, at least one of the first fluid container 136 and the second fluid container 138 may have a sampling chamber 158 associated therewith. The sampling chamber 158 may be configured for withdrawing or containing a volume of the first and/or second fluid from the first and/or second fluid container 136, 138, respectively, to test the fluid for quality control prior to use of the container. The sampling chamber 158 may be configured to allow a small sample volume of fluid to be withdrawn and tested from the first and/or second fluid container 136, 138 without contaminating the remaining contents of the first and second fluid containers 136, 138. In one embodiment, the sampling chamber 158 has a sampling tube 160 that is sealed at a distal end 162. Fluid from the first fluid container 136 or the second fluid container 138 fills the sampling tube 160. The proximal end 164 of the sampling tube 160 may then be sealed, such as by heat sealing, and the sampling tube 160 is cut off at the proximal end 164 or otherwise removed while the container and its contents remains sealed. The sampling chamber 158 is then removed and used for testing the fluid contained therein. While FIG. 7H illustrates the combination of sampling chamber 158 with the arrangement of cartridge components as shown in FIG. 7A, it is to be understood that the sampling chamber 158 may be incorporated into at least one of the fluid containers associated with any of the embodiments shown in FIGS. 6B and 7B-7H to provide fluid sampling capability to all embodiments of the cartridge 120 described herein.

While each of the embodiments of the cartridge 120 in FIGS. 6B and 7A-7H shows the pump 134, and in certain embodiments, pump 135 and valve 140 assembly provided within the cartridge 120, in other embodiments, one or more of the pump(s) and/or valve assembly may be provided outside the interior cavity of the cartridge 120. In such embodiments, the cartridge 120 may include a connection interface to connect the fluid path from the first and/or second fluid containers 136, 138 to the valve 140 and/or pump(s) 134 (and/or pump 135) provided outside the cartridge 120. One of ordinary skill in the art will appreciate that one or more of a plurality of connection interfaces may be utilized to connect the fluid path from the first and second fluid containers 136, 138 to the valve 140 and/or pump(s) 134 (and/or pump 135). In some embodiments, the cartridge 120 may include a self-contained power source 156 (shown in FIG. 6B), such as a battery pack, or it may be connected to an external power source, such as an external power outlet to power the pump(s) 134 (and/or pump 135) and/or the valve 140 and other powered components of cartridge 120 and fluid delivery system 100.

In various embodiments, one or more of the fluid connections within cartridge 120, for example between the first and second fluid containers 136, 138, the valve 140, one or more pumps 134, 135, and the multi-patient connector 116 may be made at the time of manufacture to ensure a sterile fluid path between the first and second fluid containers 136, 138 and the multi-patient connector 116. In other embodiments, one or more of the fluid connections within cartridge 120, for example between the first and second fluid containers 136, 138, the valve 140, one or more pumps 134, 135, and the multi-patient connector 116 are made after the manufacture. In such embodiments, it may be desirable to sterilize at least a portion of the fluid path between the first and second fluid containers 136, 138 and the multi-patient connector 116 prior to initial use. Additionally, the fluid delivery system 100 and the various components of cartridge 120, such as at least a portion of the fluid path between the first and second fluid containers 136, 138, the valve 140, one or more pumps 134, 135, and the multi-patient connector 116 may be configured to be primed prior to each use with a single-patient set. The priming operation purges air that may be trapped in the fluid path between the first and second fluid containers 136, 138 and the multi-patient connector 116. In some embodiments, the priming operation may be carried out continuously at a low flow rate, for example a low flow rate of saline and/or contrast, to prevent contamination of the fluid path between the first and second fluid containers 136, 138 and the multi-patient connector 116. Such a continuous purging/priming process may further prevent crystallization of the contrast when the fluid delivery system 100 is idle between patient injections. In certain embodiments, the fluid delivery system 100 may further comprise a waste receptacle (not shown) in fluid connection with at least one fluid path within cartridge 120, for example, at multi-patient connector 116, to collect any flow of purging/priming fluid.

Figure 8A:
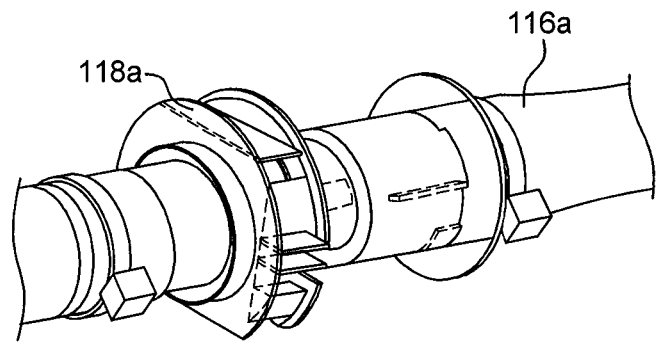
FIG. 8A is a perspective view of a connector assembly in accordance with one embodiment.
Figure 8B:
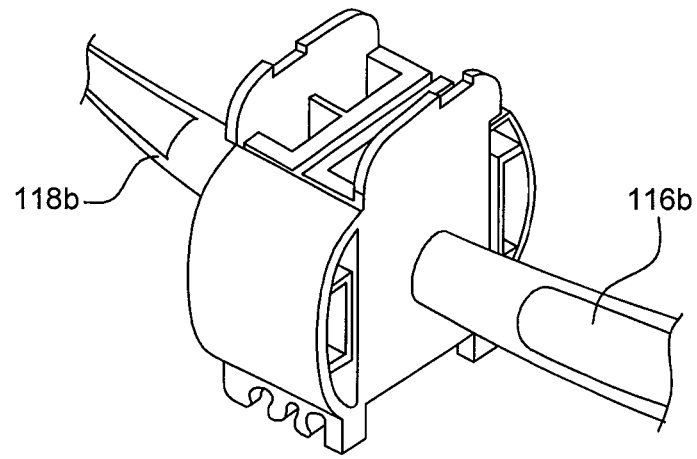
FIG. 8B is a perspective view of a connector assembly in accordance with another embodiment.
Figure 8C:
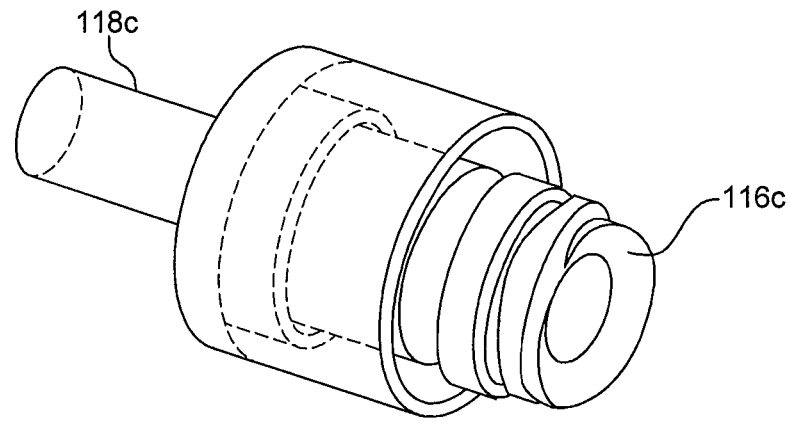
FIG. 8C is a perspective view of a connector assembly in accordance with another embodiment.

Referring to FIGS. 8A-8D, a plurality of multi-patient connectors 116a-116d and corresponding connectors 118a-118d on the single-patient connector is illustrated. In each embodiment, the multi-patient and single-patient connectors 116a-116d, 118a-118d, respectively, are configured for retaining a sterile connection therebetween. Each of the connectors may be configured for use on the connection interface 110 for connecting the fluid delivery system 100 to the single patient fluid path set 114 (shown in FIG. 3). For example, a fluid connection may be established using a luer-type connection, such as illustrated in FIG. 8C.

Figure 8D:
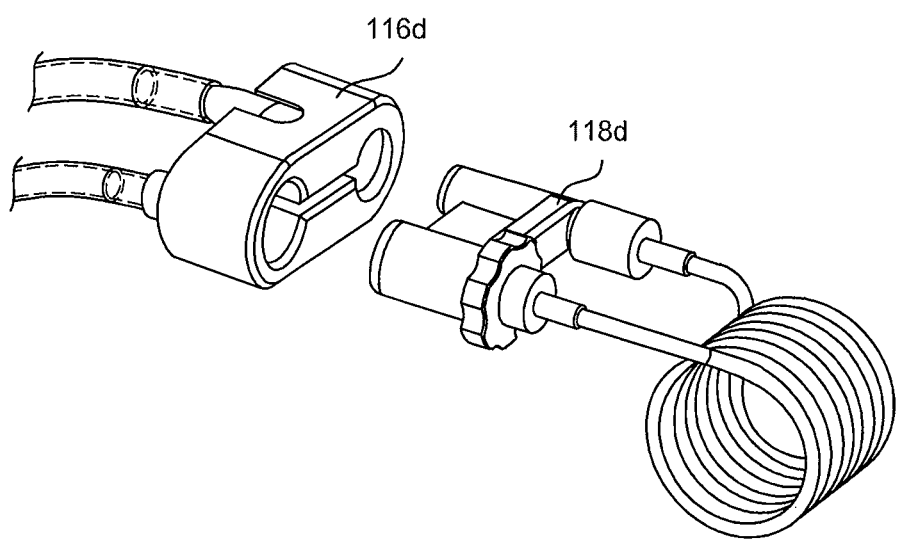
FIG. 8D is a perspective view of a connector assembly in accordance with another embodiment.

With reference to FIG. 8D, the connector assembly includes a multi-patient connector 116d having a fluid path port configured for fluid connection with the fluid delivery system 100 and a waste fluid port in fluid connection with a waste container (not shown). In some embodiments, the waste container may be provided within the cartridge 120 or the cartridge carrier 108, or it may be a separate component connectable to the fluid delivery system 100. The fluid path set 114 (for example, shown in FIGS. 3 and 6B) includes: a fluid path port removably engageable with the fluid path port of the multi-patient connector 116d to establish a fluid connection therewith; a waste fluid port removably engageable with the waste fluid port of the multi-patient connector 116d to establish a fluid connection therewith; and a patient fluid line connected, at one end, to the fluid path port of the single-patient connector 118d and removably connected, at the other end, to the waste fluid port of the single-patient connector 118d. Fluid flow through the patient fluid line 114 is unidirectional, from the end of the patient line connected to the fluid path port to the end of the patient fluid line connected to the waste fluid port. The patient fluid line is capable of being disconnected from the waste fluid port and connected to a patient catheter to establish a fluid connection from the fluid delivery system 100 (shown in FIGS. 3 and 6B) to the patient through the fluid path ports and patient fluid line. Various embodiments of the connector assembly shown in FIG. 8D are disclosed in U.S. Provisional Patent Application No. 61/925,940, filed Jan. 10, 2014, entitled "Single-Use Disposable Set Connector", and assigned to the application of the present disclosure.

Referring to FIGS. 9-20F, a medical connector assembly 10 (hereinafter "connector assembly 10") is illustrated in accordance with various embodiments of the present disclosure. The connector assembly 10 is configured for use as the connection interface 110 between the fluid delivery system 100 and the fluid path set 114 (shown in FIG. 3).

With initial reference to FIGS. 9-12, the assembled connector assembly 10, generally includes a multi-patient connector 116 and a single-patient connector 118 releasably connected to the multi-patient connector 116. In one embodiment, the multi-patient connector 116 is provided on the fluid delivery system 100 (shown in FIG. 3), such as on the cartridge 120. The single-patient connector 118 is configured for removably connecting to the multi-patient connector 116 to deliver the first fluid, the second fluid, or a mixture thereof from the fluid delivery system 100 to the patient.

The multi-patient connector 116 is desirably a hollow, tubular structure made from a material suitable for medical applications, such as medical-grade plastic. In some embodiments, the multi-patient connector 116 is constructed from a clear medical-grade plastic in order to facilitate visual verification that a fluid connection has been established with the single-patient connector 118. The multi-patient connector 116 may be formed on at least a portion of the cartridge 120. At least one multi-patient connector 116 is provided on the cartridge 120. Additionally, or in the alternative, one or more fluid path elements (not shown), such as medical tubing, a catheter, or other fluid path element, may be connected to the multi-patient connector 116 to enable fluid communication to the multi-patient connector 116. For example, in one embodiment, the multi-patient connector 116 is in fluid communication with the fluid outlet line 114 (shown in FIG. 7A). The multi-patient connector 116 desirably has one or more fluid passageways 18 configured for interfacing with the single-patient connector 118. The one or more fluid passageways 18 are configured for allowing the passage of fluid through the multi-patient connector 116 for delivery of the first fluid, the second fluid, or a mixture thereof from the fluid delivery system 100 to the patient.

Figure 9:
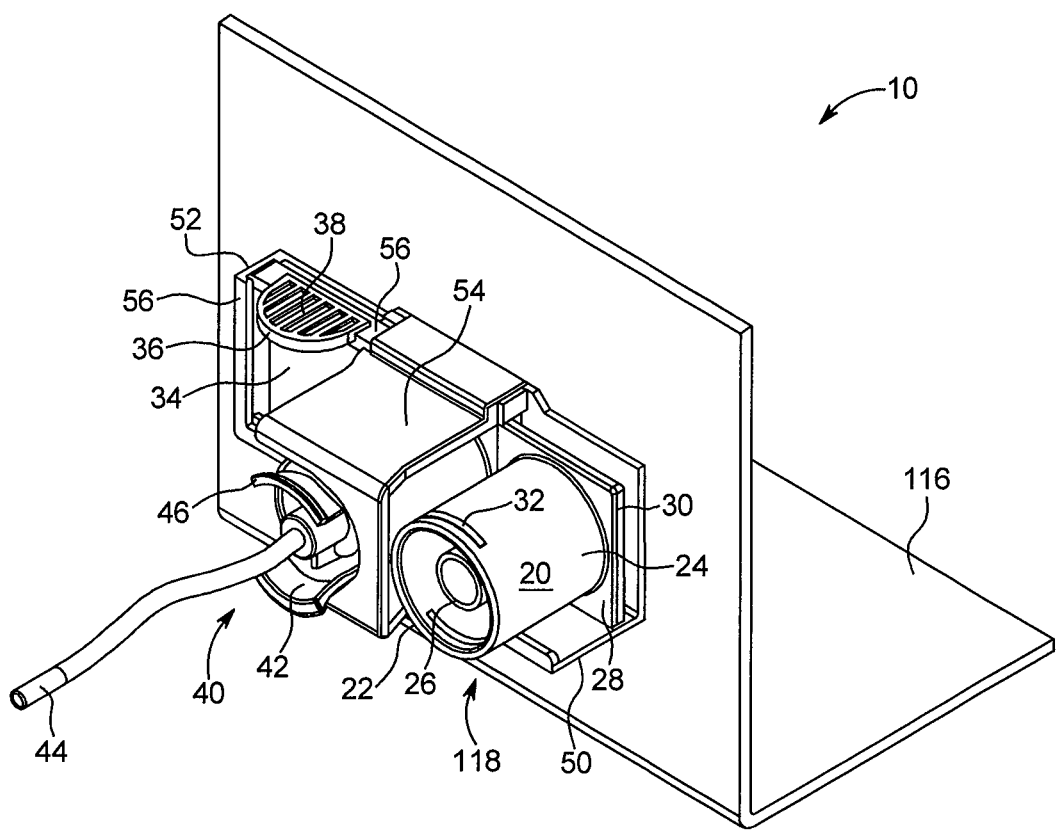
FIG. 9 is a perspective view of a connector assembly in accordance with another embodiment.
Figure 10:
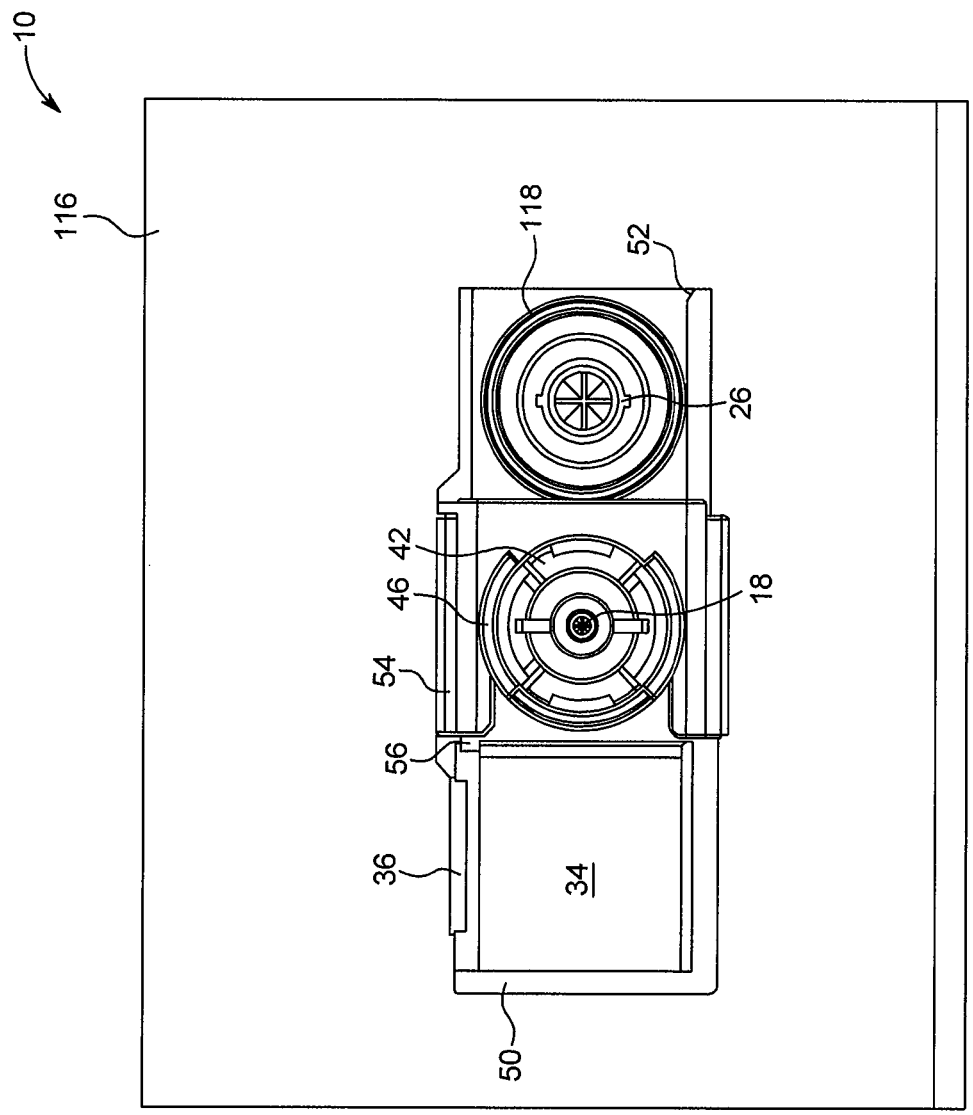
FIG. 10 is a front view of the connector assembly shown in FIG. 9.
Figure 11:
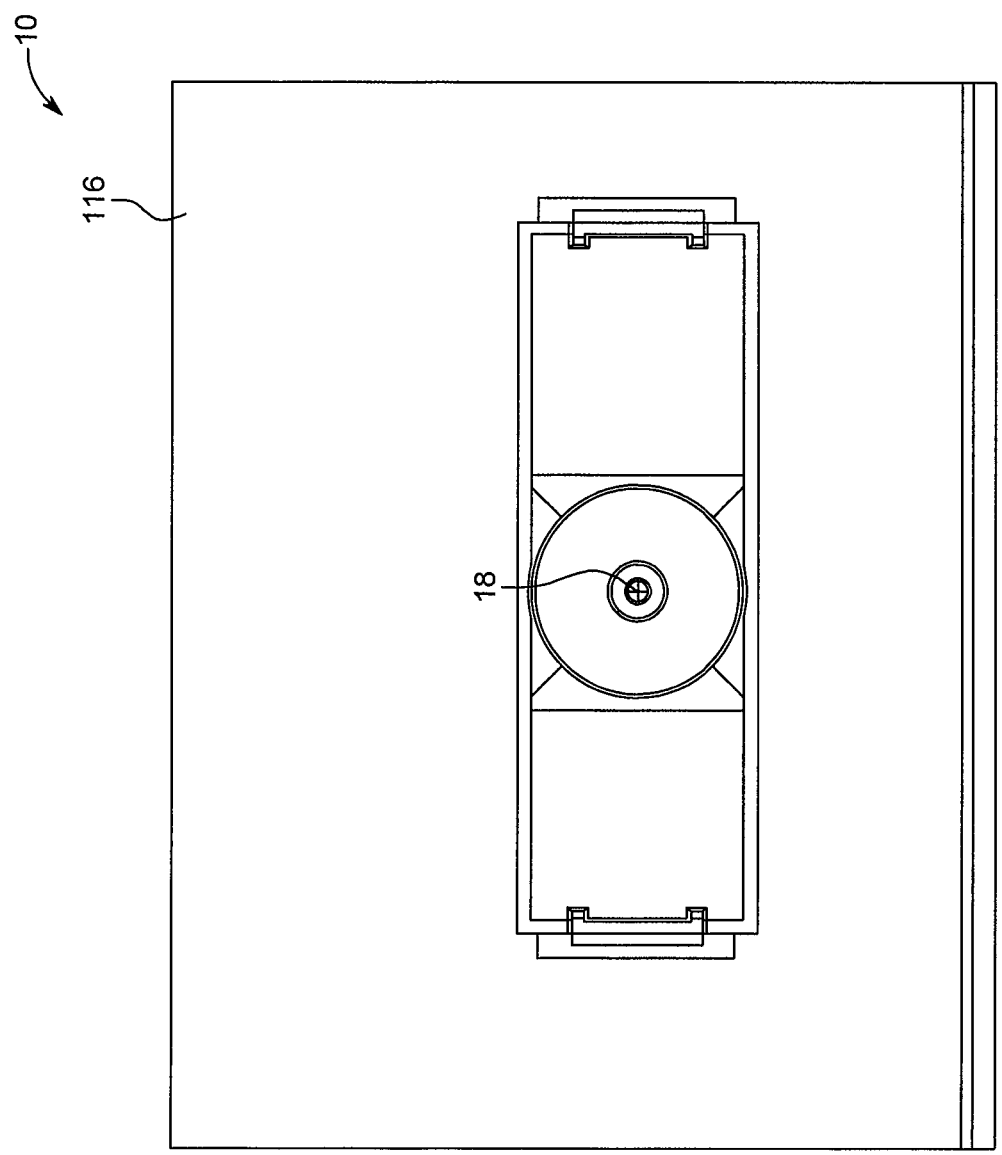
FIG. 11 is a rear view of the connector assembly shown in FIG. 9.
Figure 12:
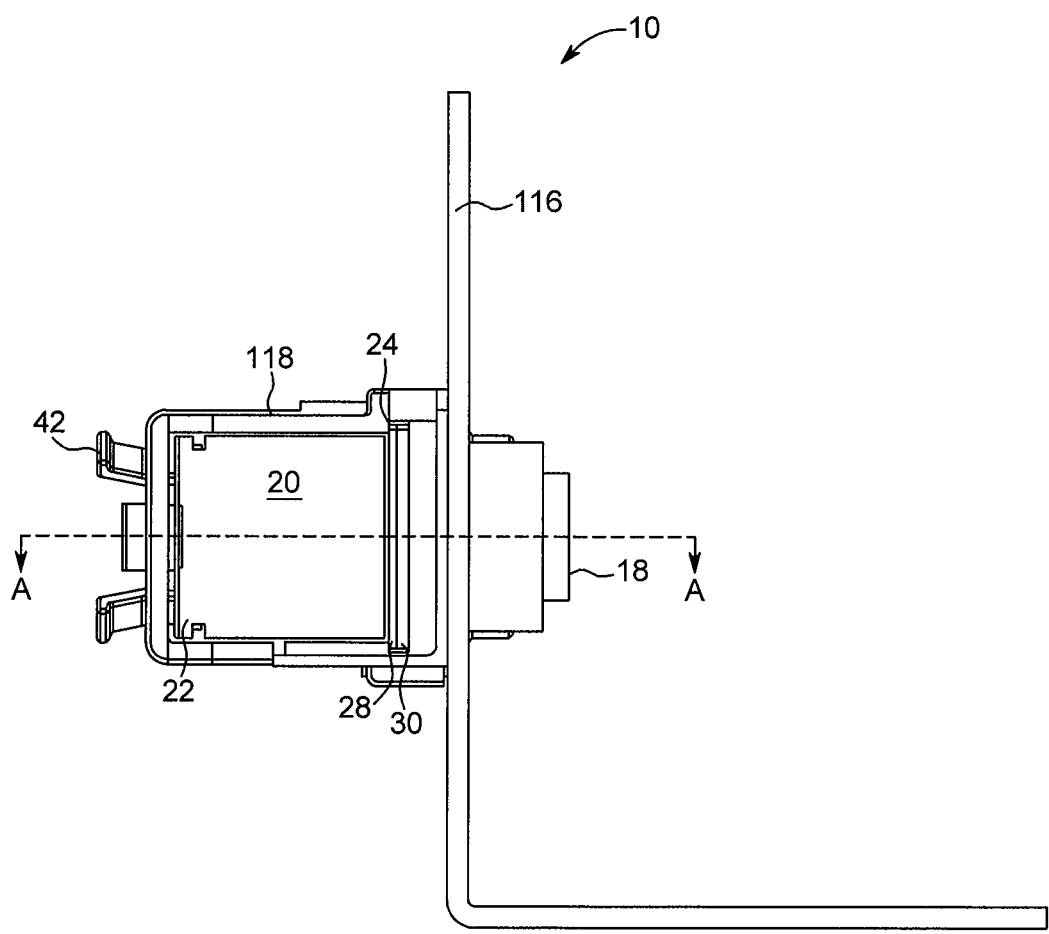
FIG. 12 is a side view of the connector assembly shown in FIG. 9.
Figure 13:
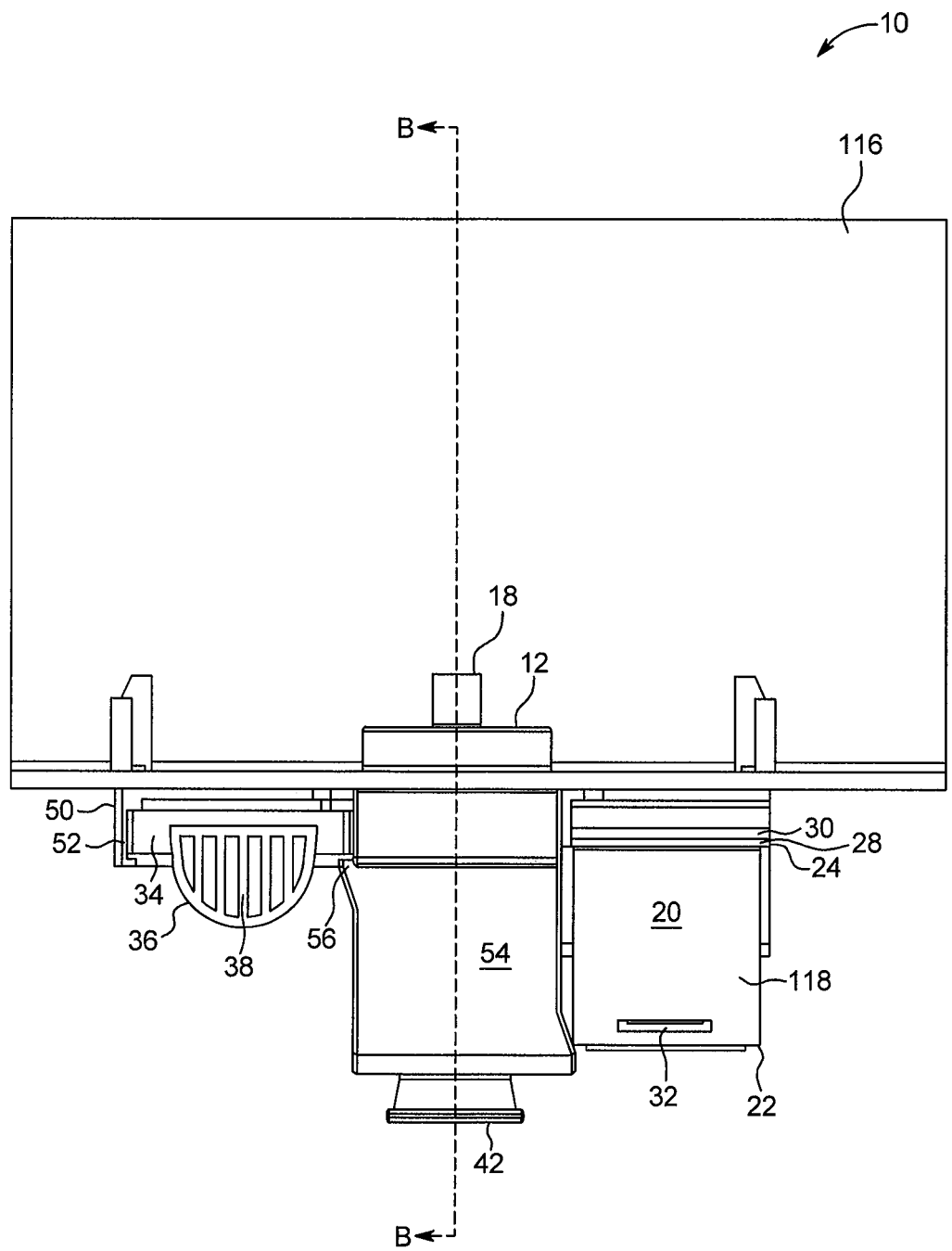
FIG. 13 is a top view of the connector assembly shown in FIG. 9.
Figure 14:
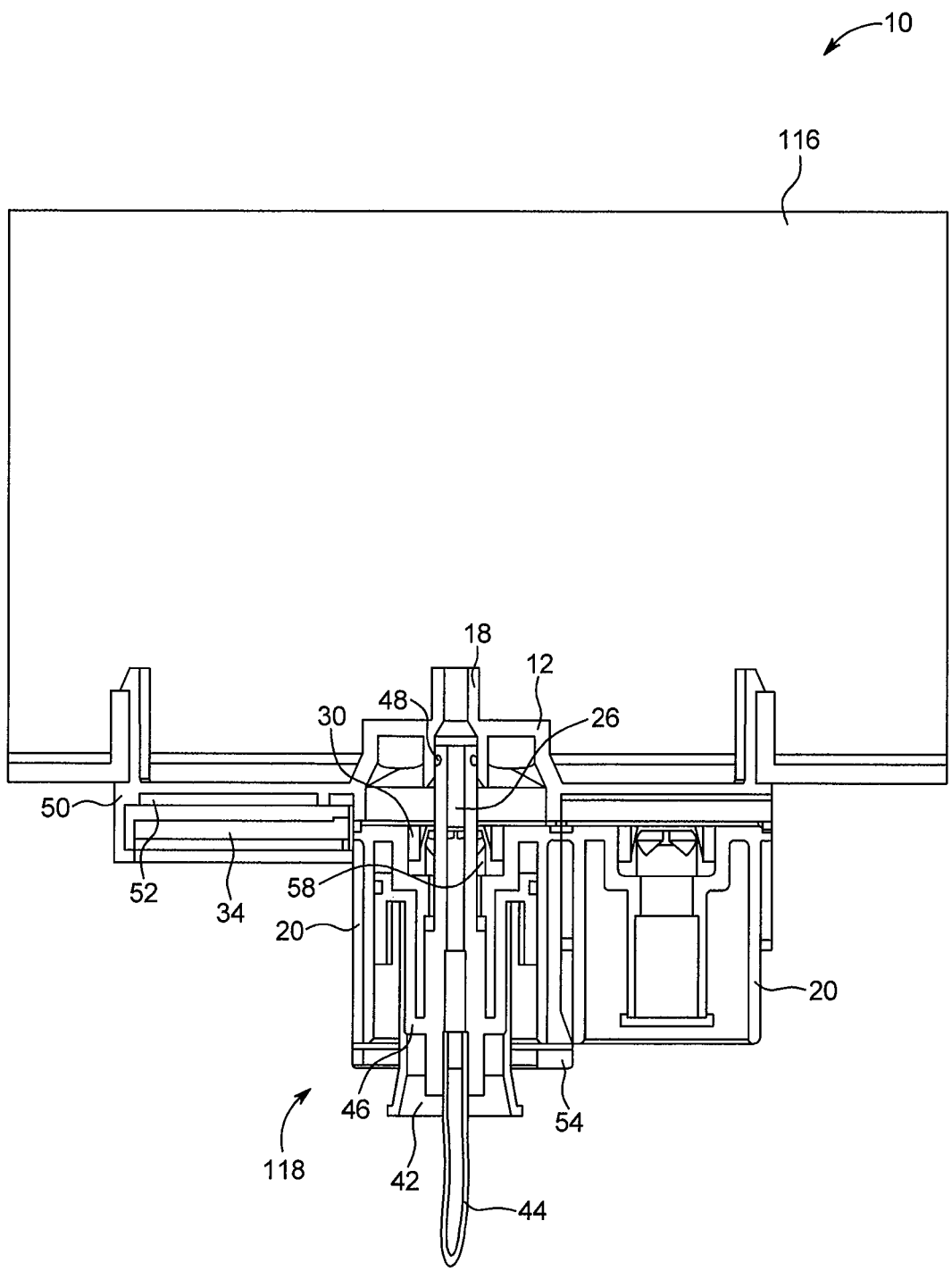
FIG. 14 is a cross-sectional view of the connector assembly taken along line A-A shown in FIG. 12.

As described in detail herein, the multi-patient connector 116 is configured for connecting to a single-patient connector 118 which is configured to be disposed after a single use. Each single-patient connector 118 is desirably a hollow, tubular structure made from a material suitable for medical applications, such as medical-grade plastic. With specific reference to FIG. 9, the connector assembly 10 is shown with one single-patient connector 118 that is connected to the multi-patient connector 116 and one single-patient connector 118 that is ready for disposal after use. Both single-patient connectors 118 are shown in FIG. 9 in a state after removal from packaging (not shown). Each single-patient connector 118 is desirably packaged in a pre-sterilized, sealed package that protects the single-patient connector 118 from contamination with air or surface-borne contaminants.

Figure 16:
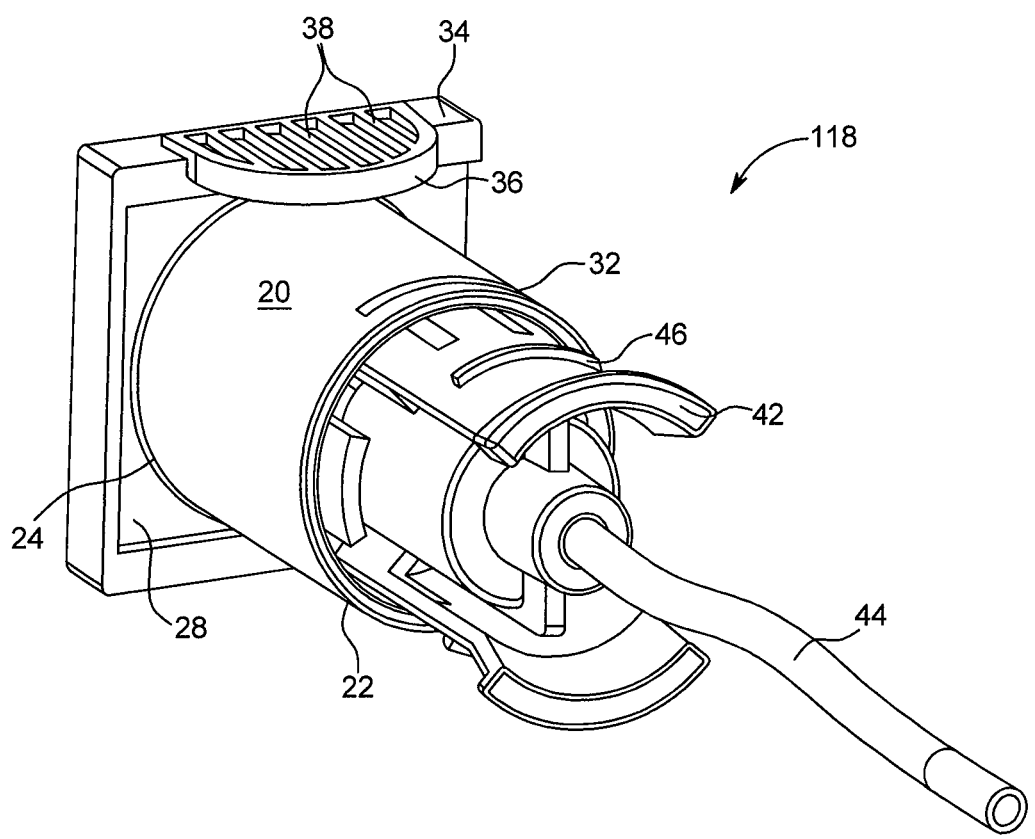
FIG. 16 is a front perspective view of a single-patient connector configured for use with the connector assembly shown in FIG. 9.
Figure 17:
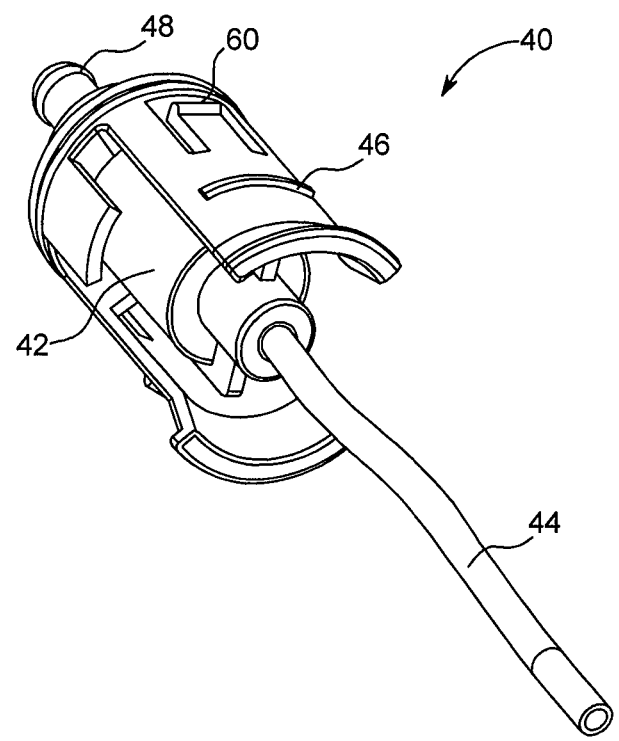
FIG. 17 is a front perspective view of a fluid path connector of the single-patient connector shown in FIG. 16.
Figure 18:
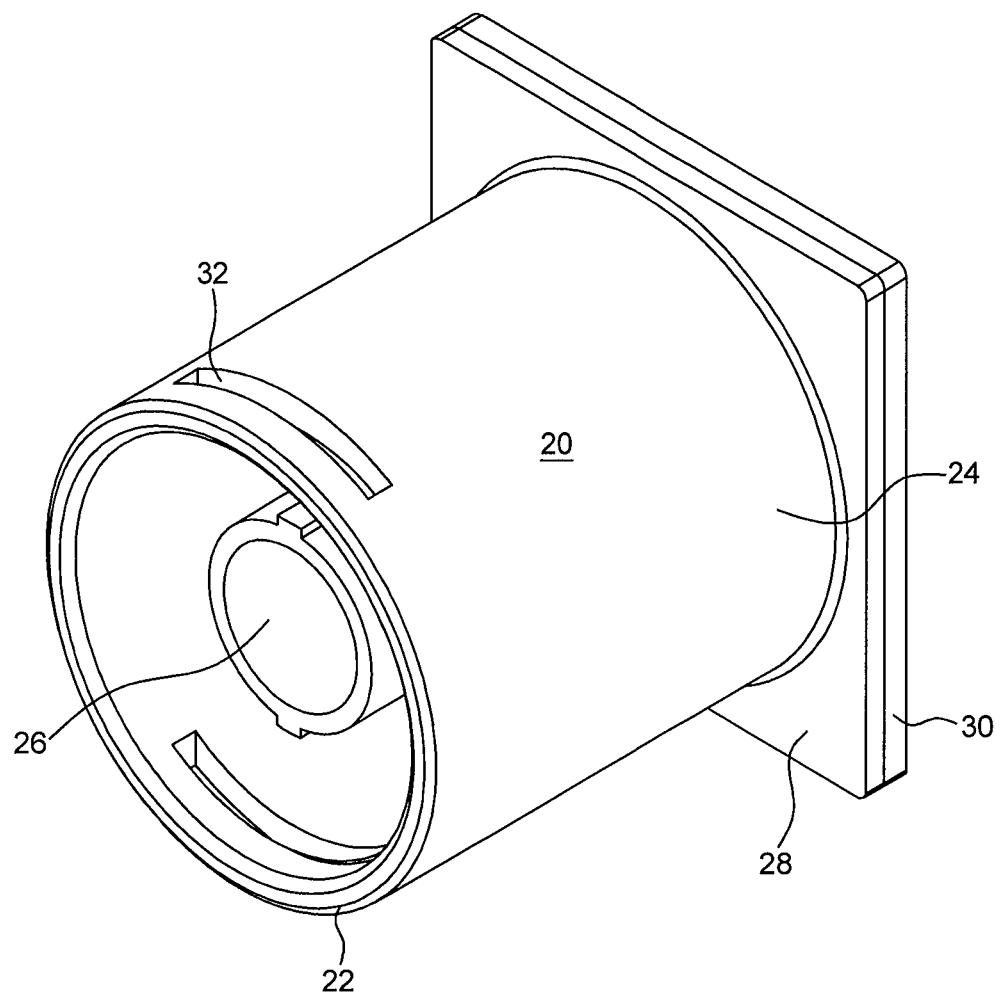
FIG. 18 is a front perspective view of a housing of the single-patient connector shown in FIG. 17.
Figure 19:
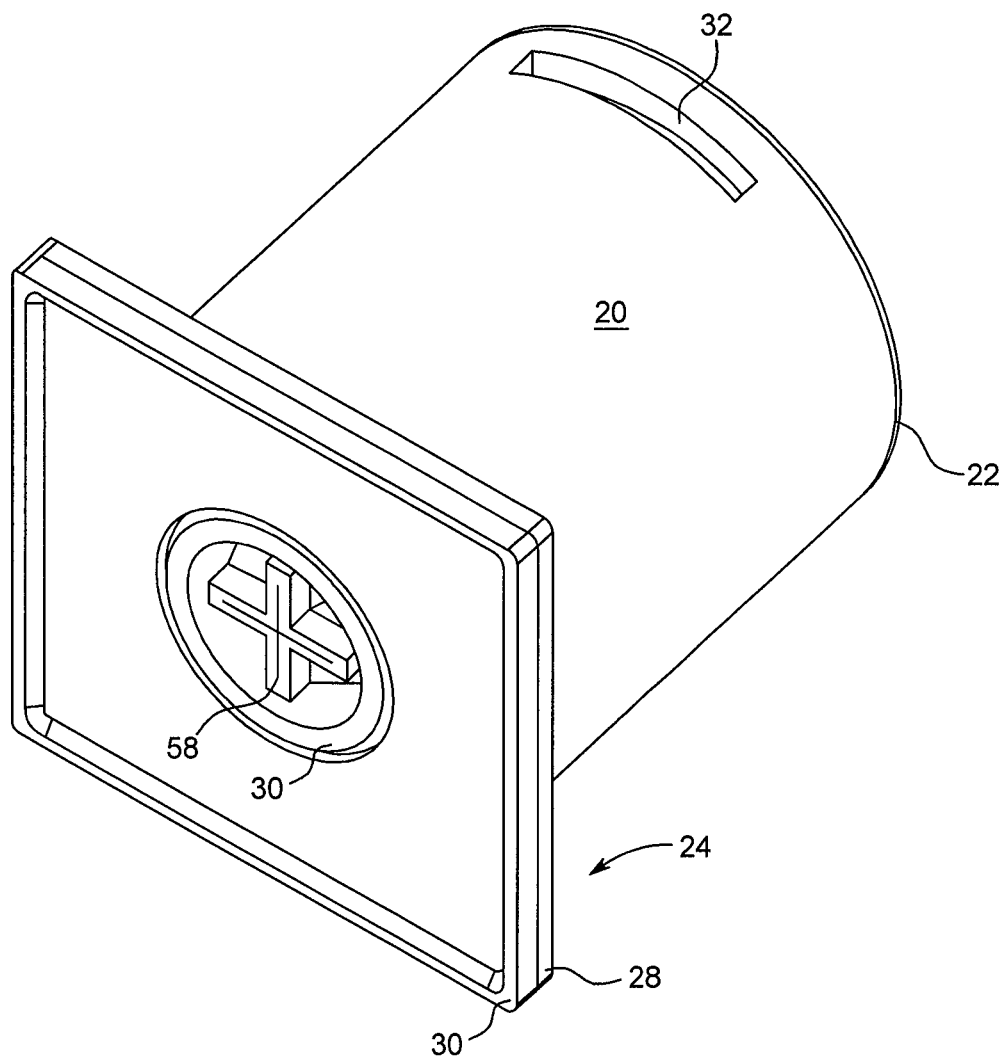
FIG. 19 is a rear perspective view of the housing shown in FIG. 18.

With reference to FIG. 9, each single-patient connector 118 includes a housing 20 having a hollow tubular form. The housing 20 has a proximal end 22 and a distal end 24 with a central fluid passage 26 extending through a longitudinal length of the housing 20 between the proximal and distal ends 22, 24. The central fluid passage 26 is desirably recessed relative to the proximal end 22 to prevent undesired contact with the central fluid passage 26. The distal end 24 of the housing 20 includes a substantially quadrilateral flange 28 that extends from the housing 20. A seal 30 is provided around a perimeter of the flange 28. The housing 20 further includes one or more recesses 32 configured for engaging a male connector of a fluid path, as will be described hereafter. Referring to FIG. 16, a cap 34 is provided on the distal end 24 of the housing 20. The cap 34 has a generally quadrilateral shape that is adapted to envelop the flange 28 of the housing 20. A finger tab 36 is provided on one or more sides of the cap 34 to facilitate removal of the cap 34 from the housing 20. The cap 34 engages the seal 30 (shown in FIG. 18) to maintain a sterile interface at the flange 28. The cap 34 is slidably mounted on the flange 28 such that it can slide substantially perpendicularly relative to the longitudinal axis of the housing 20. The finger tab 36 may have a plurality of ribs 38 on the external sidewall thereof to provide a convenient gripping surface for the user to remove the cap 34 after the single-patient connector 118 is connected to the multi-patient connector 116.

The single-patient connector 118 may be, for example, removably attached to or, alternatively, part of a syringe, fluid pump device, and like fluid delivery devices. As shown in FIG. 9, the single-patient connector 118 includes a fluid path 40 having a male connector 42 and a fluid line 44. The male connector 42 has one or more resilient tabs 46 that are configured to engage the one or more recesses 32 on the housing 20 of the single-patient connector 118. Engagement between the tabs 46 of the male connector 42 and the recesses 32 of the housing 20 creates a positive locking connection. Once inserted into the central fluid passage 26 of the housing 20, the tip of the male connector 42 extends through a second seal 58 (shown in FIGS. 15 and 19). The second seal 58 may be formed as a septum that is pierced by the tip of the male connector 42. Alternatively, the second seal 58 may have one or more deflectable elements that are deflected by the tip of the male connector 42 as it is advanced through the housing 20.

Figure 15:
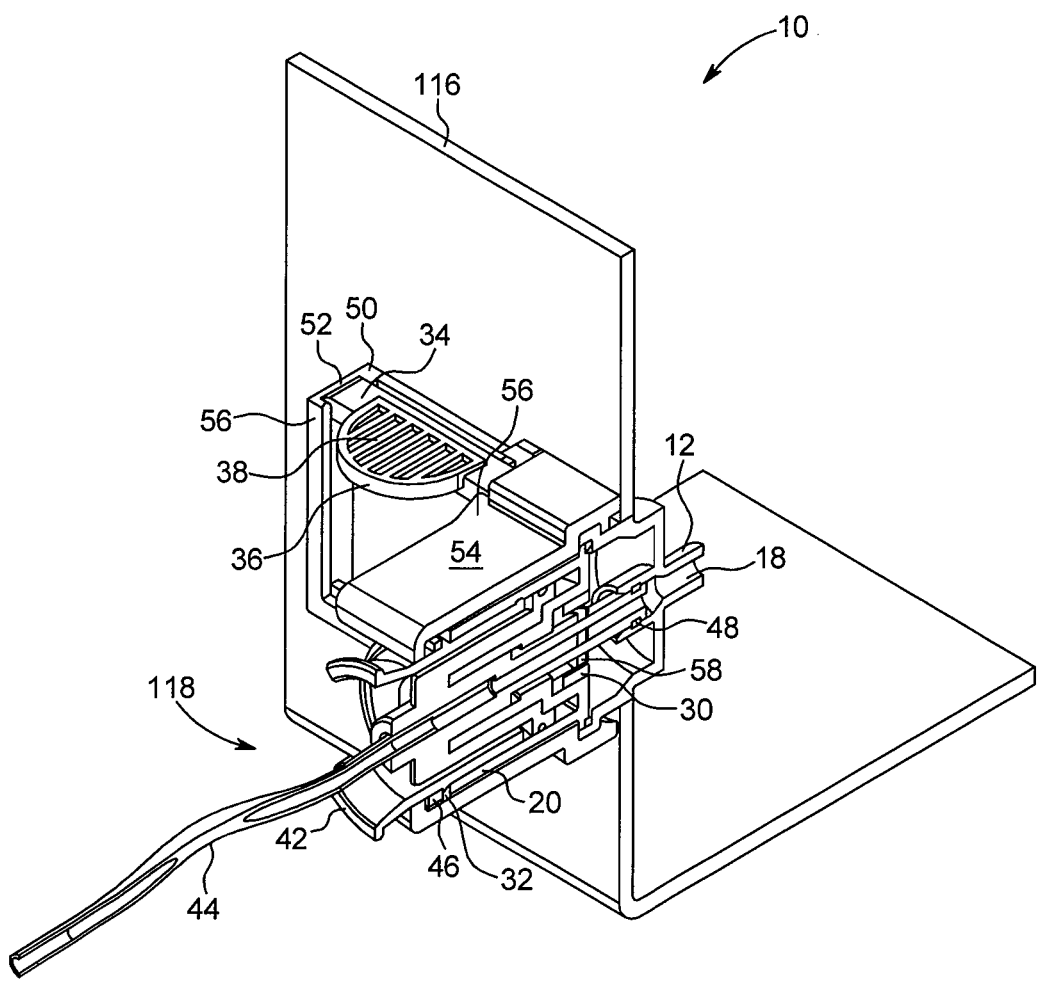
FIG. 15 is a cross-sectional view of the connector assembly taken along line B-B shown in FIG. 13.

As the male connector 42 is inserted into the housing 20, the tip of the male connector 42 interfaces with the fluid passageways 18 of the multi-patient connector 116. As shown in FIG. 15, a seal 48 is provided at the interface of the multi-patient connector 116 and the male connector 42. The seal 48 forms a fluid-tight connection between the mating elements and prevents fluid from a fluid source container, a fluid delivery device, medical tubing, etc., from dripping through the interface between the mating elements of the multi-patient connector 116 or the male connector 42. In one exemplary embodiment, the seal 48 may be an o-ring seal which is formed between a surface on the multi-patient connector 116 and a surface on the single-patient connector 118. Alternately, the seal 48 may be in the form of a face seal or an o-ring provided on the mating surface of a mating element. The mechanical connection between the multi-patient connector 116 and the male connector 42 of the fluid path 40 may be established in a number of other ways. For example, the multi-patient connector 116 may have a threaded female luer connection and the male connector 42 may have a correspondingly threaded male luer connection, or vice versa. Another alternative for making a fluid-tight connection between the multi-patient connector 116 and the male connector 42 is a bayonet connection where a male end on one of the multi-patient connector 116 or the male connector 42 has one or more pins which engage a matching slot provided on the female end of the other of the multi-patient connector 116 or the male connector 42. Other possible embodiments of mechanical connection between the multi-patient connector 116 and the male connector 42 include a face-sliding attachment, barbed fittings, collet fittings, compression fittings, clamp fittings, and bonding or breakable attachments. In another embodiment, the stem of the male connector 42 could be a needle which engages a receptacle on the housing 20 which is protected by a pierceable septum. One of ordinary skill in the art will recognize that this listing of connection alternatives for making fluid-tight connections between the mating components of the multi-patient connector 116 and the male connector 42 is not exhaustive and that other equivalent mechanical connecting arrangements may be used. Additionally, various combinations and permutations of the foregoing-described mechanical connecting arrangements may be employed in accordance with this disclosure.

Referring back to FIG. 9, the connector assembly 10 further includes a frame 50 that is adapted to slidably receive one or more single-patient connectors 118 and to support the multi-patient connector 116. In one embodiment, the frame 50 has a width that is at least an integer multiple of the width of the single-patient connector 118. The height of the frame 50 is substantially equal to the height of the cap 34 of the single-patient connector 118. In one embodiment, a plurality of single-patient connectors 118 may be disposed in a cartridge 120 for sequential loading into the frame 50. The frame 50 may be integrally formed with the cartridge 120 or it may be removably or non-removably attached thereto.

Figure 20A:
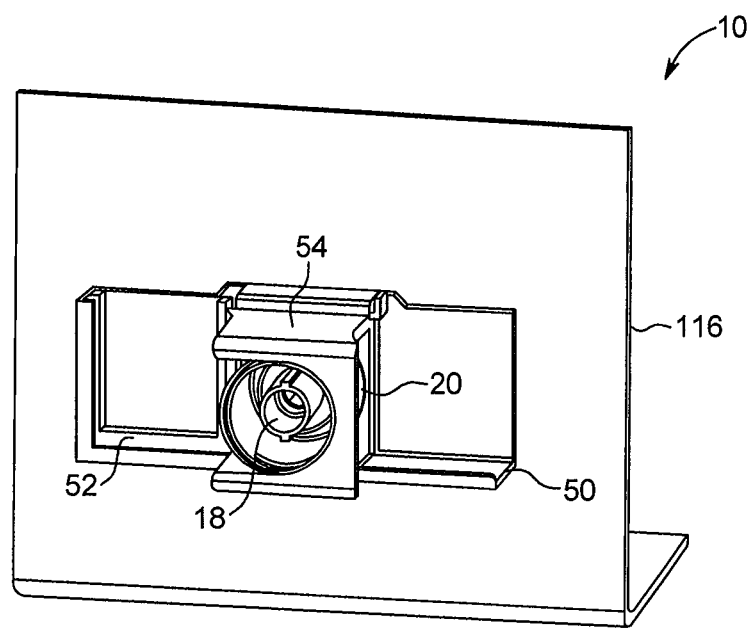
FIGS. 20A-20F are perspective views of various stages of connecting a single-patient connector to a multi-patient connector.
Figure 20B:
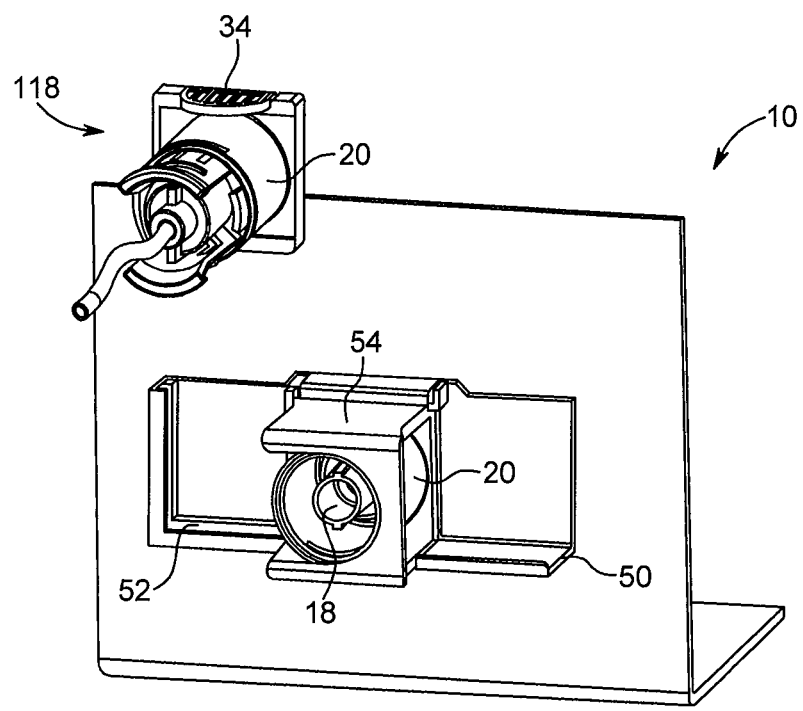
Figure 20C:
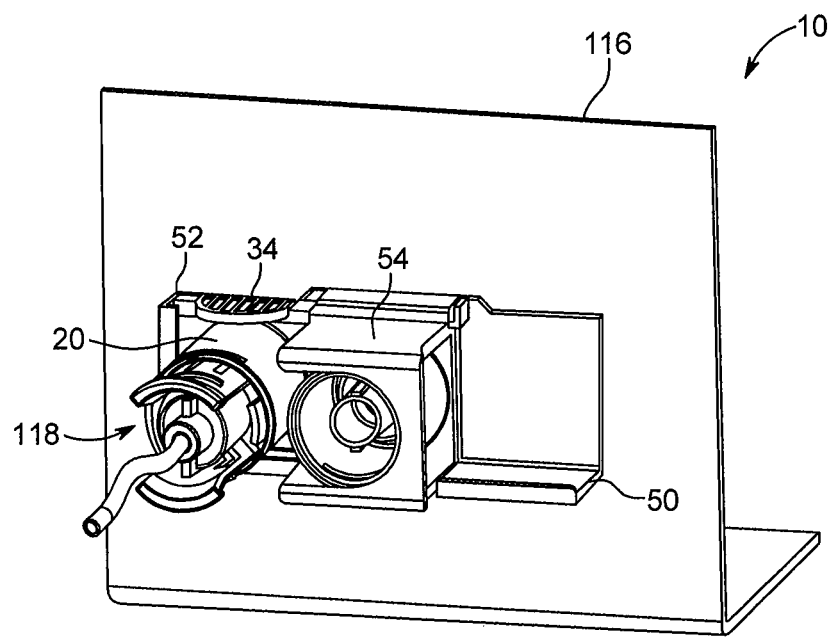

With reference to FIGS. 20A-20F, a method of using the medical connector assembly 10 will now be described. Initially, with reference to FIG. 20A, the housing 20 of the single-patient connector 118 is positioned into a groove 52 on the frame 50 such that the housing 20 is aligned with the fluid passageway 18 of the multi-patient connector 116. Such arrangement of the housing 20 protects the fluid passageway 18 of the multi-patient connector 116 from contamination. The frame 50 further includes a shroud 54 that extends opposite of the multi-patient connector 116, as shown in FIG. 20B. The shroud 54 is configured to envelop the housing 20 of the single-patient connector 118. Referring to FIGS. 20B-C, the single-patient connector 118 is inserted into the groove 52 on the frame 50 by aligning the cap 34 of the single-patient connector 118 with the groove 52 and positioning the single-patient connector 118 within the groove 52. A pair of projections 56 (shown in FIG. 9) on the shroud 54 is adapted to fixedly retain the cap 34 of the single-patient connector 118 as the single-patient connector 118 is slid within the groove 52 of the frame 50.

Figure 20D:
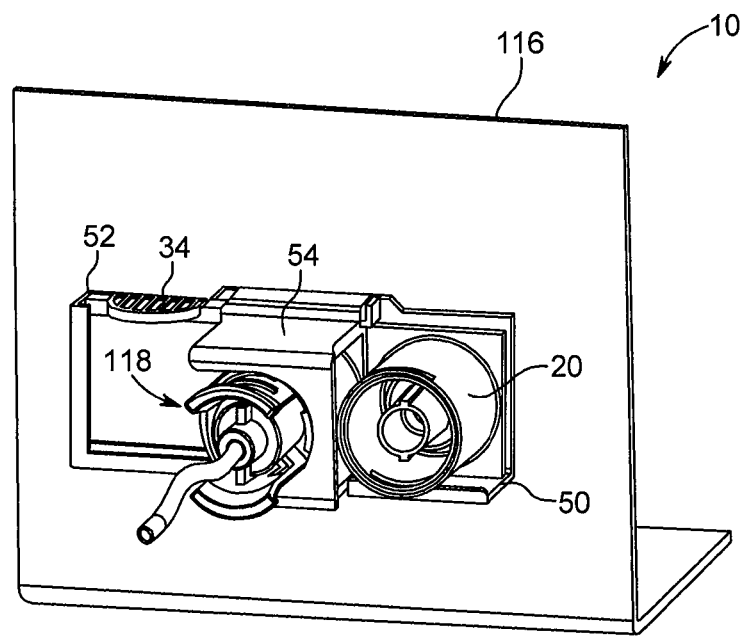
Figure 20E:
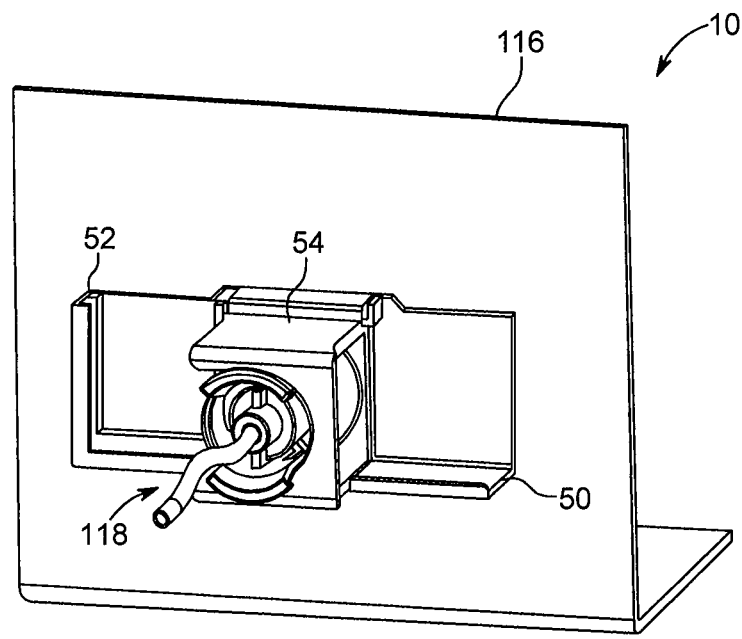

With reference to FIG. 20D, the inserted single-patient connector 118 is moved laterally toward the housing 20 that covers the fluid passageway 18 of the multi-patient connector 116. As the single-patient connector 118 slides within the shroud 54, the cap 34 is removed without exposing the distal end 24 of the housing 20 of the single-patient connector 118. Sliding of the single-patient connector 118 within the groove 52 of the frame 50 causes the seal 30 at the distal end 24 of the housing 20 to slidably engage the frame 50 to prevent contamination of the single-patient and multi-patient connectors 118, 116. In an alternative embodiment, the shroud 54 is slidable relative to the frame 50. In this embodiment, the single-patient connector 118 is loaded at one end of the shroud 54 while the shroud 54 is oriented in a first position. The shroud 54 is then moved relative to the frame 50 to bring the single-patient connector 118 in alignment with the multi-patient connector 116. After use, the single-patient connector 118 can be discarded by sliding the shroud 54 in a second position. Once the single-patient connector 118 is aligned with the multi-patient connector 116, the cap 34 and the displaced housing 20 may be removed from the frame 50 by grasping the finger tab 36 of the cap 34 and by removing the housing 20 from the frame 50, respectively (see FIG. 20D). In another embodiment, the cap 34 and the housing 20 may be automatically disposed into a receptacle (not shown). The male connector 42 is pushed into the housing 20, thereby disengaging the locking tabs 60 (see FIG. 17). Further movement of the male connector 42 into the housing 20 engages the second seal 58 and locks the resilient tabs 46 on the male connector 42 with the recesses 32 in the housing 20. In another embodiment, male connector 42 may be locked in position with threads. Once a secure, fluid-tight connection between the multi-patient connector 116 and the single-patient connector 118 is made, fluid from a fluid source or a fluid delivery device may be delivered to the fluid path 40, and either immediately or ultimately delivered to a patient as desired.

Figure 20F:
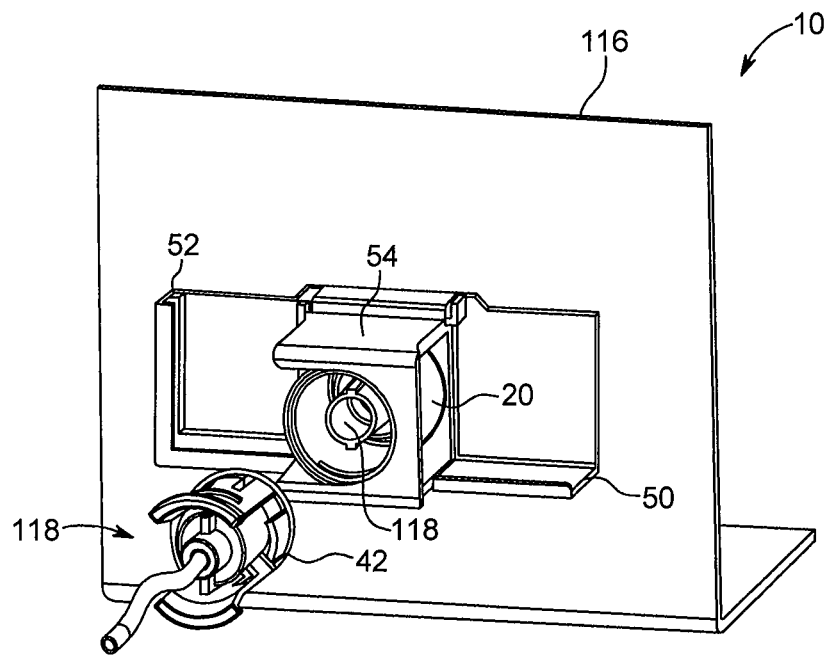

After completion of a fluid delivery procedure, the male connector 42 may be removed, leaving the housing 20 to cover the fluid passageway 18 of the multi-patient connector 116 (see FIG. 20F). When it is desired to remove the single-patient connector 118 from connection with the multi-patient connector 116, a second single-patient connector 118 is inserted into the groove 52 of the frame 50 and is moved into alignment with the multi-patient connector 116. Movement of the second single-patient connector 118 causes the first single-patient connector 118 to be displaced from connection to the multi-patient connector 116. After positioning the second second-patient connector 118 into alignment with the multi-patient connector 116, the displaced first single-patient connector 118 may be removed from the frame 50 and discarded.

Figure 21A:
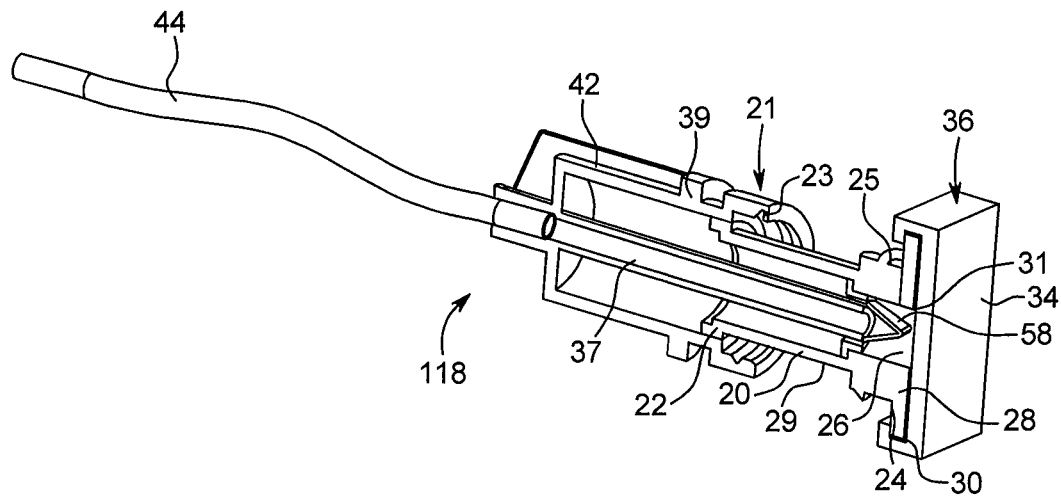
FIG. 21A is a perspective view of a single-patient connector in accordance with another embodiment.
Figure 21B:
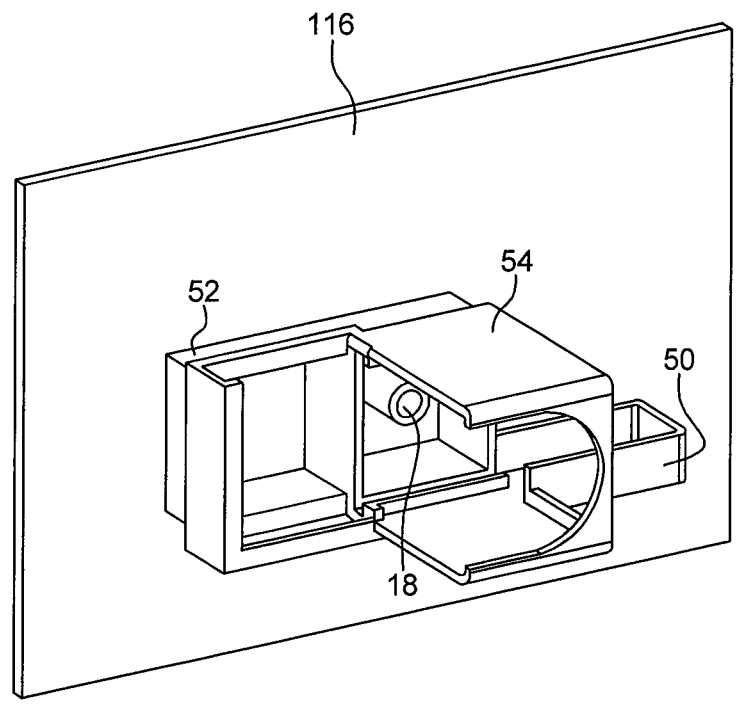
FIG. 21B is a perspective view of a multi-patient connector configured for use with the single-patient connector shown in FIG. 21A.

With reference to FIG. 21A, the single-patient connector 118 is shown in accordance with another embodiment. The single-patient connector 118 has a hollow, tubular structure made from a material suitable for medical applications, such as medical-grade plastic. The single-patient connector 118 is configured for being connected to the multi-patient connector 116 shown in FIG. 21B. The single-patient connector 118 is shown in FIG. 21A in a state after removal from packaging (not shown). Prior to initial use, the single-patient connector 118 is packaged in a pre-sterilized, sealed package that protects the single-patient connector 118 from contamination with air or surface-borne contaminants.

With continued reference to FIG. 21A, each single-patient connector 118 includes a housing 20 having a hollow tubular form. The housing 20 has a proximal end 22 and a distal end 24 with a central fluid passage 26 extending through a longitudinal length of the housing 20 between the proximal and distal ends 22, 24. The central fluid passage 26 is desirably recessed relative to the proximal end 22 to prevent undesired contact with the central fluid passage 26. The housing 20 is configured for telescopically receiving a male connector 42.

The male connector 42 includes a central channel 37 surrounded by an annular skirt 39. The central channel 37 is in fluid communication with the fluid line 44. The housing 20 includes a substantially quadrilateral flange 28 and an annular skirt 29 extending proximally from the flange 28. A central opening 31 is provided at the distal end 24 of the housing 20. A first seal 30 is provided around a perimeter of the flange 28. A second seal 58 is provided within the annular skirt 29 to seal the fluid path extending through the housing 20. In one embodiment, the second seal 58 may be formed as a septum that is pierced by the central channel 37 of the male connector 42. Alternatively, the second seal 58 may have one or more deflectable elements that are deflected by the tip of the male connector 42 as it is advanced through the annular skirt 29 of the housing 20. In another embodiment, the second seal 58 may be in a form of a dual one-way check valve arrangement.

A cap 34 is provided on the distal end 24 of the housing 20. The cap 34 has a generally quadrilateral shape that is adapted to envelop the flange 28. A finger tab 36 is provided on one or more sides of the cap 34 to facilitate removal of the cap 34 from the housing 20. The cap 34 engages the seal 30 to maintain a sterile interface at the flange 28. The cap 34 is slidably mounted on the flange 28 such that it can slide substantially perpendicularly relative to the longitudinal axis of the housing 20.

In one embodiment, the male connector 42 and the housing 20 may have a locking mechanism 21 to lock the male connector 42 and the housing 20 from moving relative to each other. For example, the male connector 42 may have a groove 23 that is received within a projection 25 provided on the housing 20. Alternatively, the groove 23 may be provided on the housing 20 while the projection 25 may be provided on the male connector 42. A pair of locking mechanisms can be provided to lock the male connector 42 relative to the housing 20 in a first position and a second position. In the first position, the male connector 42 may be positioned further apart from the housing 20 than in the second position.

Figure 22A:
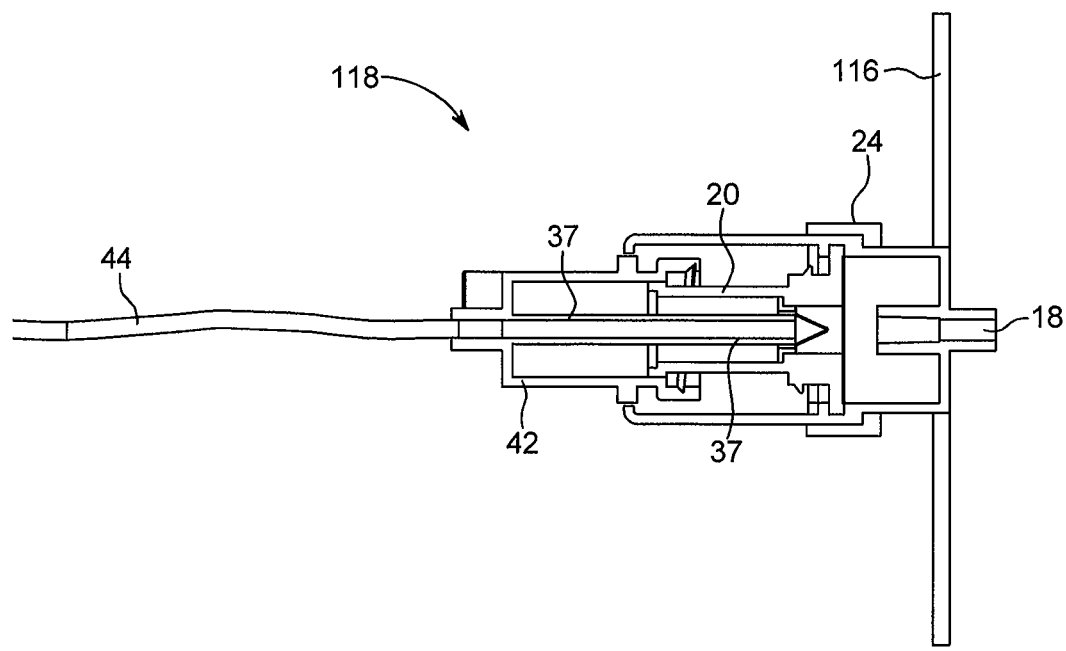
FIGS. 22A-22C are perspective views of various stages of connecting the single-patient connector of FIG. 21A to the multi-patient connector of FIG. 21B.
Figure 22B:
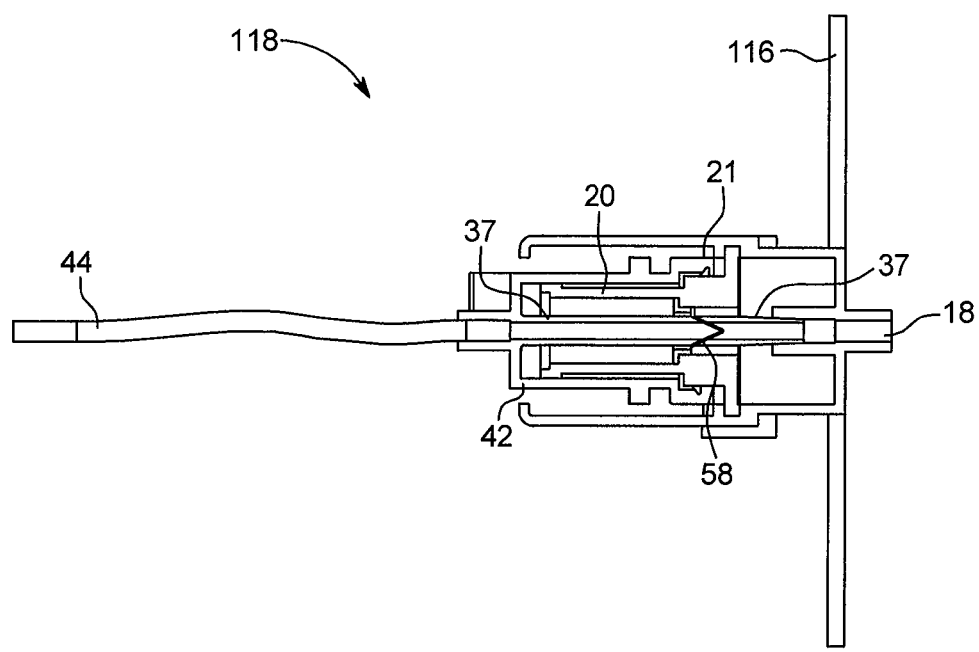

A method of using the single-patient connector 118 shown in FIG. 21A is substantially similar to the method of using the single-patient connector 118 shown in FIGS. 20A-20F. Referring initially to FIG. 22A, the single-patient connector 118 is placed in position on the multi-patient connector 116 as described hereinabove with reference to FIG. 20A-20D. The male connector 42 is pushed into the housing 20 toward the distal end 24. Further movement of the male connector 42 into the housing 20 engages the second seal 58 and locks the locking mechanism 21, as shown in FIG. 22B. In another embodiment, male connector 42 may be locked in position with threads. Once a secure, fluid-tight connection between the multi-patient connector 116 and the single-patient connector 118 is made, fluid from a fluid source or a fluid delivery device may be delivered to the fluid line 44, and either immediately or ultimately to a patient as desired.

Figure 22C:
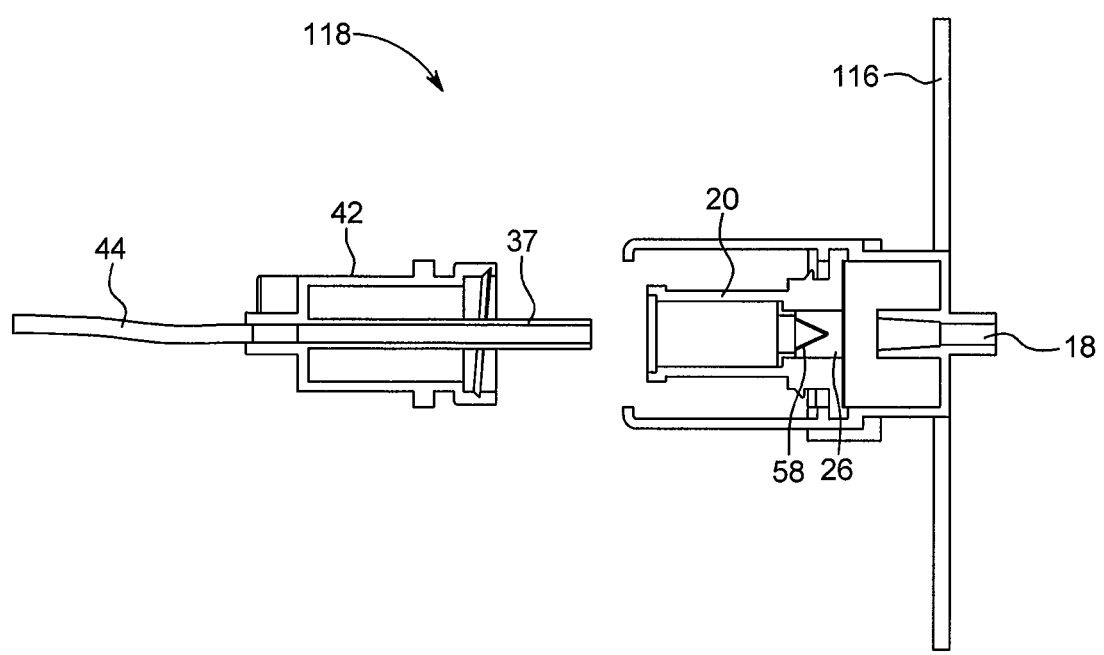

After completion of a fluid delivery procedure, the male connector 42 may be removed, leaving the housing 20 to cover the fluid passageway 18 of the multi-patient connector 116 (see FIG. 22C). When it is desired to remove the single-patient connector 118 from connection with the multi-patient connector 116, a second single-patient connector 118 is inserted into the groove 52 of the frame 50 and is moved into alignment with the multi-patient connector 116. Movement of the second single-patient connector 118 causes the first single-patient connector 118 to be displaced from connection to the multi-patient connector 116. After positioning the second single-patient connector 118 into alignment with the multi-patient connector 116, the displaced first single-patient connector 118 may be removed from the frame 50 and discarded.

Figure 23A:
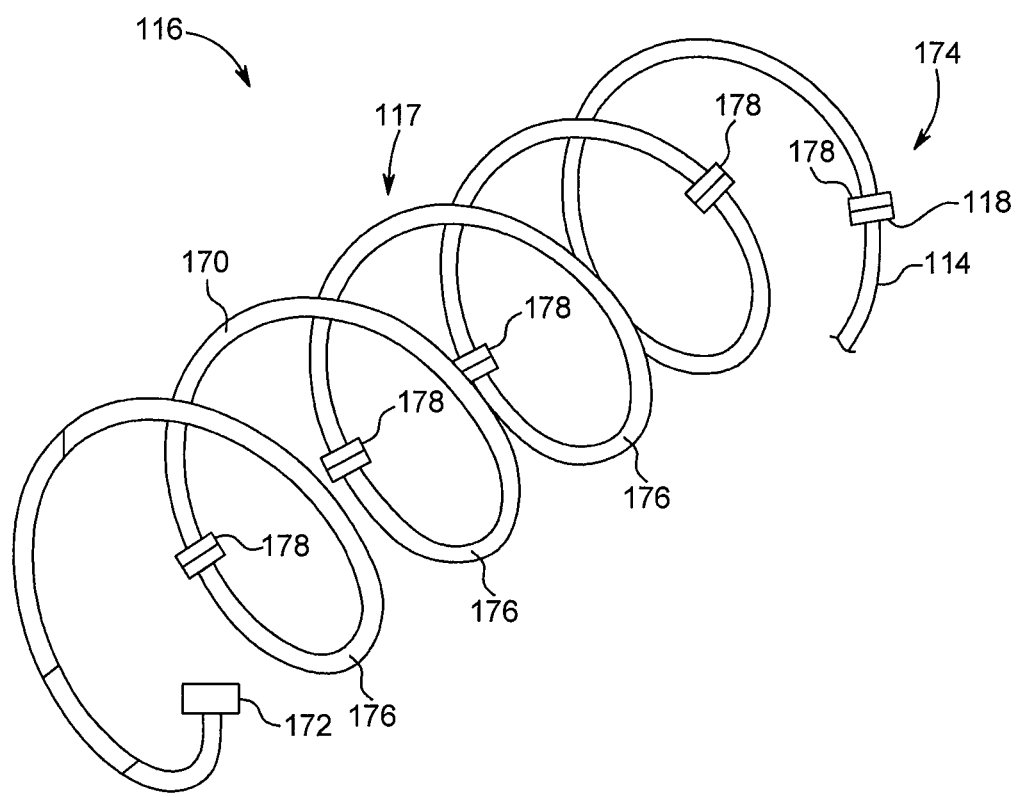
FIG. 23A is a schematic view of a first variation of a fluid outlet line of the multi-patient connector in accordance with a further embodiment.

With reference to FIG. 23A, a fluid outlet line 117 of the multi-patient connector 116 is shown in accordance with one embodiment. The fluid outlet line 117 has a generally tubular body 170 with a proximal end 172 configured for connection with the pump 134 (shown in FIGS. 7A-7H) or the valve 140 (shown in FIGS. 7A-7H) or a fluid path extending distally from pump 134. A distal end 174 is provided opposite the proximal end 172. In one embodiment, the fluid outlet line 117 may be spooled on a reel (not shown) such that the distal end 174 can be drawn out from the reel. The tubular body 170 has a plurality of tubular segments 176 connected together by connection members 178. The plurality of tubular segments 176 may be arranged serially such that a proximal end of one tubular segment 176 is connected to a distal end of an adjacent tubular segment 176 or to the fluid path set 114. The connection members 178 may have a one-way valve member that prevents the flow of fluid from the distal end 174 of the fluid outlet line 117 toward the proximal end 172 and thereby prevent contamination of the next proximal segment when the most distal segment is removed. In another embodiment, the connection members 178 have a releasable connection structure that allows the adjacent tubular segments 176 to be separated such that the distal segment may be removed and discarded, for example after a single patient use. Upon removal of the most distal segment, the next adjacent segment becomes the distal segment and may be placed in fluid connection with a patient fluid path, such as a single use patient fluid path.

In use, the connection member 178 of the distal most tubular segment 176 is configured for connection with the fluid path set 114 for delivering fluid to the patient. After priming the fluid outlet line 117 and completing an injection procedure, the fluid path set 114 is disconnected from the distal most tubular segment 176 and the distal most tubular segment 176 is disconnected from the adjacent tubular segment 176. Alternatively, the fluid path set 114 and the distal most tubular segment 176 may remain connected, while the distal most tubular segment 176 is disconnected from the adjacent tubular segment 176. In this manner, the distal most tubular segment 176 can be connected to a second fluid path set 114 for a second injector procedure. The multi-patient connector 116 can be replaced when all or substantially all of the tubular segments 176 have been used. In another embodiment, the tubular segment 176 may be cut at a proximal end of the distal-most connection member 178. The exposed end of the tubular segment 176 may then be sealed, such as by adding a fitting. The fitting can then be connected with a second fluid path set 114 for the next injection procedure.

Figure 23B:
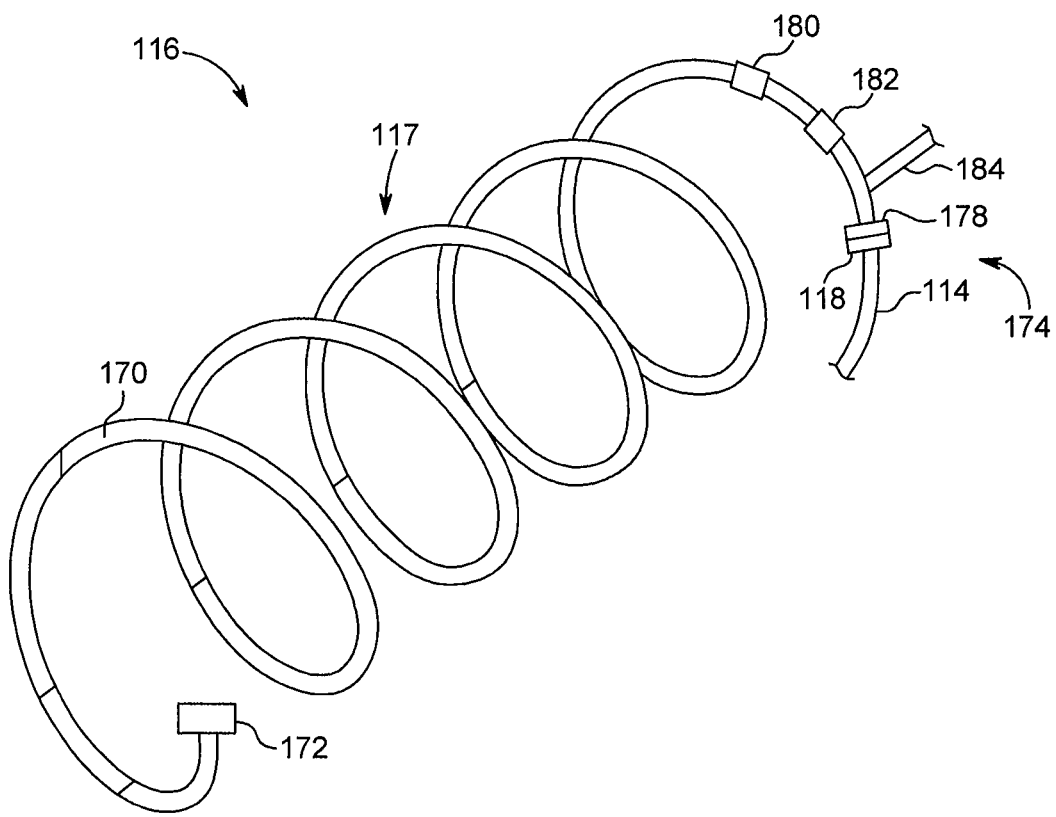
FIG. 23B is a schematic view of a second variation of a fluid outlet line of the multi-patient connector.

With reference to FIG. 23B, a fluid outlet line 117 of the multi-patient connector 116 is shown in accordance with one embodiment. The fluid outlet line 117 has a generally tubular body 170 with a proximal end 172 configured for connection with the pump 134 (shown in FIGS. 7A-7H) or the valve 140 (shown in FIGS. 7A-7H) or a fluid path extending distally from pump 134. A distal end 174 is provided opposite the proximal end 172. In one embodiment, the fluid outlet line 117 may be spooled on a reel (not shown) such that the distal end 174 can be drawn out from the reel. Prior to use, the user can draw out a desired length of the fluid outlet line 117.

With continued reference to FIG. 23B, the distal end 174 of the fluid outlet line 117 is sealed with a proximal seal 180 and a distal seal 182 that prevent fluid flow through the tubular body 170 of the fluid outlet line 117. Prior to use, a cut is made between the proximal seal 180 and the distal seal 182 such that the distal portion of the tubular body 170 is cut off from the rest of the fluid outlet line 117 and the proximal portion of the tubular body 170 is sealed by the proximal seal 180. The exposed end of the tubular body 170 is then connected to a connection member 178 (shown in FIG. 24) to facilitate connection with the fluid path set 114. In another embodiment, the exposed end of the tubular body 170 may be inserted over or into the proximal end of the fluid path set 114 and the connection therebetween can be established by heat or adhesive sealing the interface between the tubular body 170 and the fluid path set 114. Once connected with the fluid path set 114, an injector needle 184 pierces the sidewall of the tubular body 170 between the proximal seal 180 and the connection member 178 to deliver fluid to the patient. Tubular body 170 comprises a plurality of proximal seals 180 and distal seals 182 spaced along the length of the tubular body 170 each at a predetermined distance from the next proximally adjacent pair of seals. After the completion of the injection procedure, the tubular body 170 is sealed with a second seal at a location proximate of the proximal seal 180. The tubular body 170 can then be cut between the second seal and the proximal seal 180 to connect a second connection member 178 to the exposed end of the tubular body 170.

Figure 24:
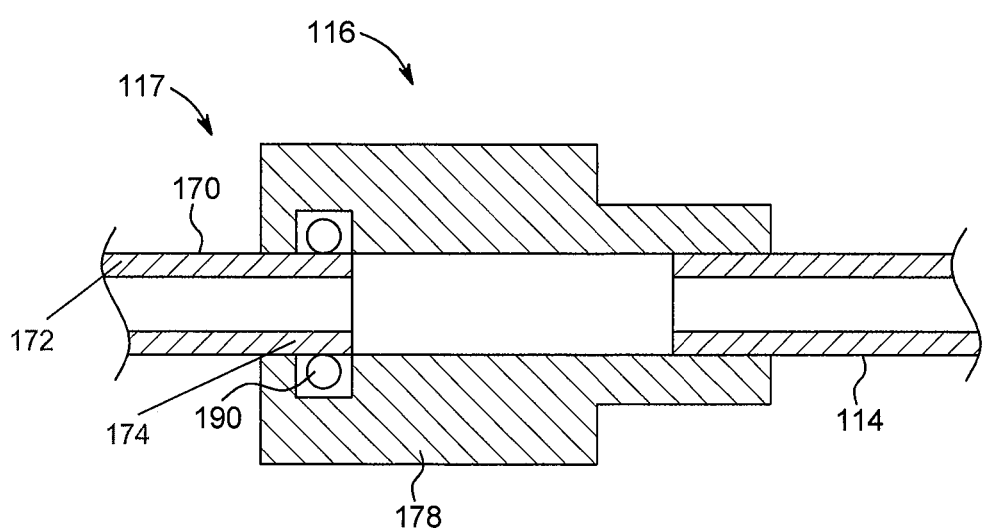
FIG. 24 is a schematic view of a connection member for use with the multi-patient connector shown in FIG. 23B in accordance with another embodiment.

With reference to FIG. 24, a fluid outlet line 117 of the multi-patient connector 116 is shown in accordance with another embodiment. The fluid outlet line 117 has a generally tubular body 170 with a proximal end 172 configured for connection with the pump 134 (shown in FIGS. 7A-7H) or the valve 140 (shown in FIGS. 7A-7H). A distal end 174 is provided opposite the proximal end 172. In one embodiment, the fluid outlet line 117 may be spooled on a reel (not shown) such that the distal end 174 can be drawn out from the reel. The distal end 174 of the fluid outlet line 117 is configured for being connected to a connection member 178. In one embodiment, the connection member 178 is part of the fluid path set 114 and may be bonded, adhered, sealed, threadably coupled, or otherwise connected with the fluid path set 114. The distal end 174 of the tubular body 170 may be inserted over or into the connection member 178. A seal 190, such as an O-ring, may be provided at the interface between the tubular body 170 and the connection member 178.

In use, the distal end 174 of the tubular body 170 of the fluid outlet line 117 is inserted into the connection member 178. In this manner, the fluid outlet line 117 is in fluid communication with the fluid path set 114 via the connection member 178. In some embodiments, the connection interface between the fluid outlet line 117 and the connection member 178 may be sealed, such as by heat sealing. After priming the fluid outlet line 117 and completing an injection procedure, the fluid outlet line 117 is disconnected from the fluid path set 114 by cutting of the distal end 174 of the fluid outlet line 117. In some embodiments, the distal end 174 may be removed from the connection member 178 before being cut. For the next injection procedure, the fluid outlet line 117 can be connected to the connection member 178 of a new fluid path set 114.

While various embodiments of the fluid delivery system 100 and the connector assembly therefor were provided in the foregoing description, those skilled in the art may make modifications and alterations to these embodiments without departing from the scope and spirit of the disclosure. For example, it is to be understood that this disclosure contemplates that, to the extent possible, one or more features of any embodiment can be combined with one or more features of any other embodiment. Accordingly, the foregoing description is intended to be illustrative rather than restrictive.

The invention claimed is:
1. A medical connector assembly, comprising:
a multi-use connector having a front face and a first fluid passageway; and
one or more single-use connectors removably engagable with the multi-use connector, each of the single-use connectors comprising:
a housing having a proximal end opposite a distal end with a central passage extending therebetween along a longitudinal axis;
a connector element removably connected within the central passage of the housing and having a second fluid passageway extending along the longitudinal axis of the housing, the connector element movable within the central passage of the housing in a direction along the longitudinal axis between a first position where the first fluid passageway of the multi-use connector is in fluid communication with the second fluid passageway of the connector element and a second position where the first fluid passageway of the multi-use connector is out of fluid communication with the second fluid passageway of the connector element;
a flange formed on the housing and extending around at least a portion of the distal end of the housing; and
a cap removably engaged to the flange,
wherein each single-use connector is slidable relative to the front face of the multi-use connector via a groove on a frame of the multi-use connector in a direction perpendicular to the longitudinal axis to align the second fluid passageway of the connector element with the first fluid passageway of the multi-use connector,
wherein the frame includes a shroud configured to envelop the housing and as one of the single-use connectors is slid within the shroud, the cap is removed by the shroud without exposing the distal end of the housing;

wherein each single-use connector comprises a first lock and a second lock, wherein the first lock reversibly locks the connector element of the respective single-use connector in the first position and the second lock reversibly locks the connector element of the respective single-use connector in the second position; and wherein the first and second locks comprise mating resilient tabs and recesses provided on either the connector element or the housing.

2. The medical connector assembly of claim 1, wherein each of the single-use connectors further comprising at least one seal, the at least one seal disposed on the flange, and wherein the at least one seal is configured to enable sliding engagement with the front face of the multi-use connector.

3. The medical connector assembly of claim 1, wherein the cap of each of the single-use connectors further comprises a tab for facilitating removal of the cap from each single-use connector.

4. The medical connector assembly of claim 1, wherein the multi-use connector further comprises at least one projection configured for disengaging and retaining the cap of the one or more single-use connectors, as the respective single-use connector is slidably moved relative to the front face of the multi-use connector.

5. The medical connector assembly of claim 1, wherein the second fluid passageway of each single-use connector comprises at least one sealing member configured for sealing the first fluid passageway when the connector element of the respective single-use connector is in the second position.

6. The medical connector assembly of claim 1, wherein at least a portion of the medical connector assembly is constructed from a medical grade plastic material.

7. The medical connector assembly of claim 1, wherein the connector element of each of the single-use connectors further comprises a tip configured for extending through the first fluid passageway of the multi-use connector and providing a fluid path between the first fluid passageway and the second fluid passageway when the connector element is in the first position.

8. The medical connector assembly of claim 7, wherein each of the single-use connectors further comprising an annular seal around the tip for sealing the fluid path between the first fluid passageway and the second fluid passageway.

9. A medical connector assembly, comprising:
a multi-use connector having a front face and a first fluid passageway; and
one or more single-use connectors removably engagable with the multi-use connector, each of the single-use connectors comprising:
a housing having a proximal end opposite a distal end with a central passage extending therebetween along a longitudinal axis;
a flange formed on the housing and extending around at least a portion of the distal end of the housing;
at least one seal on the flange;
a cap removably engaged to the flange and contacting the at least one seal to maintain a sterile interface at the flange; and
a connector element removably connected within the central passage of the housing and having a second fluid passageway extending along the longitudinal axis of the housing, the connector element movable within the central passage of the housing in a direction along the longitudinal axis between a first position where the first fluid passageway of the multi-use connector is in fluid communication with the second fluid passageway of the connector element and a second position where the first fluid passageway of the multi-use connector is out of fluid communication with the second fluid passageway of the connector element, wherein each single-use connector is slidable relative to the front face of the multi-use connector via a groove on a frame of the multi-use connector in a direction perpendicular to the longitudinal axis to align the second fluid passageway of the connector element with the first fluid passageway of the multi-use connector wherein the frame includes a shroud configured to envelop the housing and as one of the single-use connectors is slid within the shroud, the cap is removed by the shroud without exposing the distal end of the housing;

wherein each single-use connector comprises a first lock and a second lock, wherein the first lock reversibly locks the connector element of the respective single-use connector in the first position and the second lock reversibly locks the connector element of the respective single-use connector in the second position; and wherein the first and second locks comprise mating resilient tabs and recesses provided on either the connector element or the housing.

10. The medical connector assembly of claim 9, wherein the connector element of each of the single-use connectors further comprises a tip configured for extending through the first fluid passageway of the multi-use connector and providing a fluid path between the first fluid passageway and the second fluid passageway when the connector element of the respective single-use connector is in the first position.

11. A medical connector assembly, comprising:
a multi-use connector having a front face and a first fluid passageway; and
one or more single-use connectors removably engagable with the multi-use connector, each of the single-use connectors comprising:
a housing having a proximal end opposite a distal end with a central passage extending therebetween along a longitudinal axis;
a connector element removably connected within the central passage of the housing and having a second fluid passageway extending along the longitudinal axis of the housing, the connector element movable within the central passage of the housing in a direction along the longitudinal axis between a first position where the first fluid passageway of the multi-use connector is in fluid communication with the second fluid passageway of the connector element and a second position where the first fluid passageway of the multi-use connector is out of fluid communication with the second fluid passageway of the connector element;
a flange formed on the housing and extending around at least a portion of the distal end of the housing; and
a cap removably engaged to the flange, wherein each single-use connector is slidable relative to the front face of the multi-use connector via a groove on a frame of the multi-use connector in a direction perpendicular to the longitudinal axis to align the second fluid passageway of the connector element with the first fluid passageway of the multi-use connector, wherein each single-use connector is slidable relative to the front face of the multi-use connector via a groove in a direction perpendicular to the longitudinal axis to align the second fluid passageway of the connector element with the first fluid passageway of the multi-use connector, wherein the frame includes a shroud configured to envelop the housing and as one of the single-use connectors is slid within the shroud, the cap is removed by the shroud without exposing the distal end of the housing;

wherein each single-use connector comprises at least one lock that reversibly locks the connector element of the respective single-use connector in at least one of the first position and the second position; and wherein the at least one lock comprises mating resilient tabs and recesses provided on either the connector element or the housing.

12. The medical connector assembly of claim 11, wherein each of the single-use connectors further comprising at least one seal, the at least one seal disposed on the flange, and wherein the at least one seal is configured to enable sliding engagement with the front face of the multi-use connector.

13. The medical connector assembly of claim 11, wherein the cap of each of the single-use connectors further comprises a tab for facilitating removal of the cap from each single-use connector.

14. The medical connector assembly of claim 11, wherein the multi-use connector further comprises at least one projection configured for disengaging and retaining the cap of the one or more single-use connectors, as the respective single-use connector is slidably moved relative to the front face of the multi-use connector.

15. The medical connector assembly of claim 11, wherein the second fluid passageway of each single-use connector comprises at least one sealing member configured for sealing the first fluid passageway when the connector element of the respective single-use connector is in the second position.

16. The medical connector assembly of claim 11, wherein at least a portion of the medical connector assembly is constructed from a medical grade plastic material.

17. The medical connector assembly of claim 11, wherein the connector element of each of the single-use connectors further comprises a tip configured for extending through the first fluid passageway of the multi-use connector and providing a fluid path between the first fluid passageway and the second fluid passageway when the connector element is in the first position.

18. The medical connector assembly of claim 17, wherein each of the single-use connectors further comprising an annular seal around the tip for sealing the fluid path between the first fluid passageway and the second fluid passageway.

19. A medical connector assembly, comprising:
a multi-use connector having a front face and a first fluid passageway; and
one or more single-use connectors removably engagable with the multi-use connector, each of the single-use connectors comprising:
a housing having a proximal end opposite a distal end with a central passage extending therebetween along a longitudinal axis;
a flange formed on the housing and extending around at least a portion of the distal end of the housing;
at least one seal on the flange;
a cap removably engaged to the flange and contacting the at least one seal to maintain a sterile interface at the flange; and
a connector element removably connected within the central passage of the housing and having a second fluid passageway extending along the longitudinal axis of the housing, the connector element movable within the central passage of the housing in a direction along the longitudinal axis between a first position where the first fluid passageway of the multi-use connector is in fluid communication with the second fluid passageway of the connector element and a second position where the first fluid passageway of the multi-use connector is out of fluid communication with the second fluid passageway of the connector element,
wherein each single-use connector is slidable relative to the front face of the multi-use connector via a groove on a frame of the multi-use connector in a direction perpendicular to the longitudinal axis to align the second fluid passageway of the connector element with the first fluid passageway of the multi-use connector
wherein the frame includes a shroud configured to envelop the housing and as one of the single-use connectors is slid within the shroud, the cap is removed by the shroud without exposing the distal end of the housing;
wherein each single-use connector comprises at least one lock that reversibly locks the connector element of the respective single-use connector in at least one of the first position and the second position; and
wherein the at least one lock comprises mating resilient tabs and recesses provided on either the connector element or the housing.

20. The medical connector assembly of claim 9, wherein the connector element of each of the single-use connectors further comprises a tip configured for extending through the first fluid passageway of the multi-use connector and providing a fluid path between the first fluid passageway and the second fluid passageway when the connector element of the respective single-use connector is in the first position.

* * * * *